United States Patent [19]

Kleinman et al.

[11] Patent Number: 4,948,913

[45] Date of Patent: Aug. 14, 1990

[54] RENIN INHIBITORS CONTAINING 5-AMINO-2,5-DISUBSTITUTED-4-HYDROXYPENTANOIC ACID RESIDUES

[75] Inventors: Edward F. Kleinman; Robert L. Rosati; Jasjit S. Bindra, all of Groton, Conn.

[73] Assignee: Pfizer Inc., New York, N.Y.

[21] Appl. No.: 336,697

[22] Filed: Nov. 2, 1987

Related U.S. Application Data

[60] Division of Ser. No. 858,324, Apr. 30, 1986, Pat. No. 4,729,985, which is a continuation-in-part of Ser. No. 764,168, Aug. 8, 1985, abandoned.

[51] Int. Cl.$^5$ .......................................... C07C 125/065
[52] U.S. Cl. .................................... 560/115; 260/404; 560/28; 560/29; 560/160
[58] Field of Search ................. 560/125, 160, 29, 115, 560/28; 260/404

[56] References Cited

U.S. PATENT DOCUMENTS

| | | | |
|---|---|---|---|
| 4,487,963 | 12/1984 | Bock | 560/160 |
| 4,803,292 | 2/1989 | Ohfune | 560/160 |
| 4,814,485 | 3/1989 | Descamps | 560/125 |

*Primary Examiner*—Michael L. Shippen
*Attorney, Agent, or Firm*—Peter C. Richardson; J. Trevor Lumb; Robert K. Blackwood

[57] ABSTRACT

A series of novel polypeptide derivatives, containing 5-amino-2,5-disubstituted-4-hydroxypentanoic acid residues, which are useful for inhibiting the angiotensinogen-cleaving action of the enzyme renin. Particularly valuable precursors for many of these compounds are certain other 5-amino-2,5-disubstituted-4-hydroxypentanoic acid derivatives.

3 Claims, No Drawings

RENIN INHIBITORS CONTAINING 5-AMINO-2,5-DISUBSTITUTED-4-HYDROXYPENTANOIC ACID RESIDUES

CROSS REFERENCE TO RELATED APPLICATION

This is a division of application Ser. No. 858,324, filed on Apr. 30, 1986, now U.S. Pat. No. 4,729,985 which is a continuation in part of application Ser. No. 764,168, filed Aug. 8, 1985, now abandoned.

BACKGROUND OF THE INVENTION

The present invention is concerned with a series of novel polypeptide derivatives containing 5-amino-2,5-disubstituted-4-hydroxypentanoic acid residues, which are useful for inhibiting the angiotensinogencleaving action of the enzyme renin; and intermediates therefor, particularly N-alpha-[N-(t-butoxycarbonyl)-phenylalanyl]-N(imidazole)-(t-butoxycarbonyl)histidine.

The proteolytic enzyme renin, which has a molecular weight of about 40,000, is produced in and secreted into the blood by the kidney. It is known to be active in vivo in cleaving the naturally-occurring plasma glycoprotein angiotensinogen. In the case of human angiotensinogen, cleavage is at the bond between the leucine (10th) and valine (11th) amino acid residues at the N-terminal end of the angiotensinogen:

Asp-Arg-Val-Tyr-Ile-His-Pro-Phe-His-Leu-Val- 1  2  3  4  5  6  7  8  9  10  11

Ile-His-Ser-Glu- 12  13  14  15

The circulating N-terminal decapeptide (angiotensin I) formed by the above cleaving action of renin is subsequently broken down by the body to an octapeptide known as angiotensin II. Angiotensin II is known to be a potent pressor substance, i.e. a substance that is capable of inducing a significant increase in blood pressure, and is believed to act by causing the constriction of blood vessels and the release of the sodium-retaining hormone aldosterone from the adrenal gland. Thus, the renin-angiotensinogen system has been implicated as a causative factor in certain forms of hypertension.

One means of alleviating the adverse effects of the functioning of the renin-angiotensinogen system is the administration of a substance capable of inhibiting the angiotensinogen-cleaving action of renin. A number of such substances are known, including antirenin antibodies, pepstatin and naturally-occurring phospholipid compounds. European Patent Application No. 77,028 discloses a series of renin-inhibiting polypeptide compounds having a non-terminal statine (Sta; 4-amino-3-hydroxy-6-methylheptanoic acid) or statine derivative. Including Sta, the vast majority of compounds exemplified contain 6 or more aminoacid residues. Exemplary of the few shortest chains there disclosed are:

Acetyl-Phe-His-Sta-Leu-Phe-NH$_2$, and t-Butyloxycarbonyl-Phe-His-Sta-Leu-Phe-NH$_2$.

There are invariably at least two amino acid residues each side of statine. The di- or polypeptidyl-statyl group is invariably attached to a lipophilic amino acid, most often leucine. (See also U.S. Pat. Nos. 4,470,971 and 4,478,826).

European Patent Application No. 45,665 and U.S. Pat. No. 4,424,207 disclose a series of renin-inhibiting polypeptide derivatives of the formula

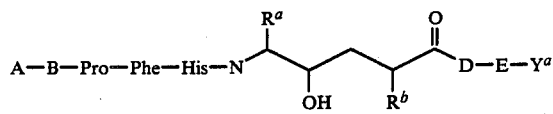

where A is for example t-butoxycarbonyl, B is His or other basic aminoacyl group, D is Val, Ile or other liphophilic aminoacyl residue, E is Tyr, Phe, His or other aromatic aminoacyl residue, $R^a$ and $R^b$ are each isopropyl, isobutyl, benzyl or other lipophilic aminoacid type sidechain, and $Y^a$ is a terminal acid, ester or amide type group. Including the central 5-aminopentanoic acid residues, these compounds are invariably heptapeptides, i.e., N-tetrapeptidyl-5-aminopentanoyl-lipophilic aminoacyl-aromatic amino-acid derivatives.

SUMMARY OF THE INVENTION

We have now discovered that certain novel compounds possess exceptional value as renin-inhibiting agents. These compounds are polypeptide derivatives of the formula

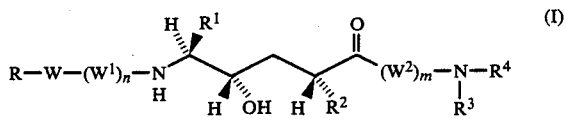

or a pharmaceutically acceptable salt thereof, wherein
n and m are each 1 or 0, the sum of n and m being at least 1;
W is

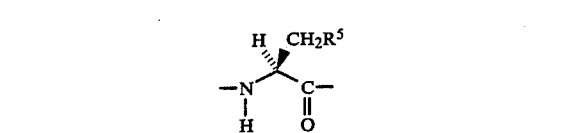

where $R^5$ is phenyl, 1-naphthyl, 4-hydroxyphenyl, 4-methoxyphenyl, 4-imidazolyl, propyl or isopropyl;

$W^1$ is

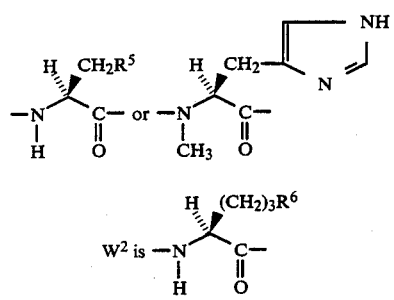

where
$R^6$ is —NH$_2$,

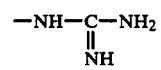

or —CH$_2$NH$_2$;

when n is 1, R is hydrogen, an amino-protecting acyl moiety having a molecular weight of less than 500, prolyl, pyroglutamyl, or prolyl or pyroglutamyl protected on nitrogen with said amino-protecting acyl moiety; and when n is O, R is phenoxyacetyl or 2-benzyl-3-phenylpropionyl (dibenzylacetyl);

R$^1$ and R$^2$ are each independently hydrogen, (C$_1$-C$_6$)alkyl, (C$_1$-C$_6$)alkenyl, phenyl, naphthyl, (C$_4$-C$_7$)cycloalkyl (C$_4$-C$_7$) cycloalkenyl, (C$_7$-C$_9$)phenylalkyl, (C$_{11}$-C$_{13}$)naphthylalkyl, (C$_5$-C$_{10}$) (cycloalkyl)alkyl, (C$_5$-C$_{10}$) (cycloalkenyl)alkyl, or one of said groups mono- or disubstituted on the aromatic ring with the same or different groups selected from (C$_1$-C$_3$)alkyl, (C$_1$-C$_3$)alkoxy, fluoro or chloro; and (a) R$^3$ and R$^4$ are taken separately, and are each independently hydrogen, (C$_1$-C$_6$)alkyl, phenyl, naphthyl, (C$_4$-C$_7$)cycloalkyl, adamantyl, (C$_7$-C$_9$)phenylalkyl, (C$_{11}$-C$_{13}$)naphthylalkyl, (C$_5$-C$_{10}$) (cycloalkyl)alkyl or adamantyl; or R$^3$ is hydrogen and R$^4$ is

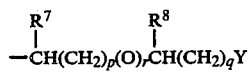

p and q are each independently zero or an integer from 1 to 6;

r is 0 or 1

Q is —CH$_2$—, —CH=CH—, —O—, —NH—, —CHOH— or —CO—;

Y is methyl, phenyl, —COOR$^9$, —CONR$^9$R$^{10}$, —CONHCOOCH$_2$C$_6$H$_5$, NH$_2$, —NHCOCH$_2$C$_6$H$_5$,

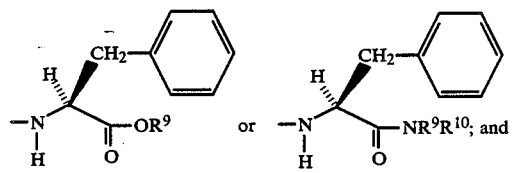

R$^7$, R$^8$, R$^9$ and R$^{10}$ are each independently hydrogen, (C$_1$-C$_6$)alkyl, phenyl, (C$_4$-C$_7$)cycloalkyl, (C$_7$-C$_9$)phenylalkyl, (C$_5$-C$_{10}$)(cycloalkyl)alkyl, or adamantyl; or (b) R$^3$ and R$^4$ are taken together with the nitrogen to which they are attached to form a pyrrole, indoline, isoindoline, piperidine, 1,2,3,4-tetrahydroquinoline, 1,2,3,4-tetrahydroisoquinoline, perhydroazepine, or morpholine ring system.

The expression "amino-protecting acyl moieties" refers to those acyl groups that are capable of substantially inhibiting reaction at the alpha-nitrogen of W (or W$^1$ when n=0) in vivo. R has a molecular weight of less than 500 in order to prevent an excessive detrimental effect on solubility characteristics. Examples of suitable amino-protecting acyl moieties are well known to those skilled in the art, e.g. the t-butyloxycarbonyl, t-butylacetyl, benzyloxycarbonyl, t-butyluriedo, (tris-hydroxy)-(t-butyluriedo) and phenoxyacetyl moieties.

When n is 1 the preferred value of R is t-butoxycarbonyl, and the preferred values of W and W$^1$ are phenylalanyl and histidyl, respectively. When m is 1, the preferred value of W$^2$ is lysyl. In all cases, the preferred value of R$^1$ is cyclohexylmethyl and the preferred values of R$^2$ are 2-methylpropyl, benzyl 2-methylpropenyl, 4-chlorobenzyl, 4-methylbenzyl, 4-methoxybenzyl, 3,4-dichlorobenzyl, 2-chlorobenzyl, 3-chlorobenzyl and cyclohexylmethyl, particularly 2-methylpropyl. When m is 0 and n is 1, the preferred values of NR$^3$R$^4$ are NH$_2$, NHCH$_3$, N(CH$_3$)$_2$, NHCH$_2$C$_6$H$_5$, NH(CH$_2$)$_3$COOH, NH(CH$_2$)$_4$NH$_2$, NH(CH$_2$)$_4$NHCOCH$_2$H$_6$H$_5$, and tetrahydroisoquinoline. When m and n are each 1, the preferred values of NR$^3$R$^4$ are phenylalanine and statine ethyl ester.

The expression pharmaceutically acceptable salt refers to acid addition salts of any of the compounds of the formula (I) which contain a basic functionality with an acid such as (but not limited to) HCl, HNO$_3$, H$_2$SO$_4$, H$_3$PO$_4$, CH$_3$SO$_3$H, pCH$_3$b C$_6$H$_4$SO$_3$H, CH$_3$COOH or HOOCCH$_2$CH$_2$COOH. When the compound (I) contains more than one basic function, the salt optionally contains more than one equivalent of acid. Alternatively, when the compound of the formula I contains an acidic function, the expression also refers to cationic salts such as, but not limited to, an alkali metal salt (e.g., Na, K), an alkaline earth salt (e.g., Ca, Mg) or an amine salt (e.g. diethanolamine, meglumine). Conventional methods are used to prepare such salts.

The present invention also encompasses pharmaceutical compositions containing a renin inhibiting-effective amount of a compound of the formula (I) as the essential active ingredient in a pharmaceutically acceptable carrier; and a method for inhibiting the cleavage of angiotensinogen by renin in the body of a mammal which comprises administering to the mammal an effective amount of a compound of the formula (I). Additionally, the present invention includes intermediate compounds of the formula

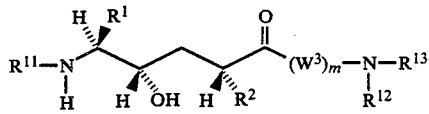

(II)

wherein
R$^1$ and R$^2$ are as defined above;
W$^3$ is

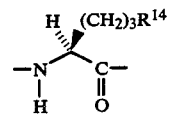

where
R$^{14}$ is —NHCO$_2$CH$_2$CH$_2$C$_6$H$_5$,

—NHCNHCO$_2$CH$_2$C$_6$H$_5$
  ||
  NH or —CH$_2$NHCO$_2$C$_6$H$_5$;

R$^{11}$ is hydrogen or t-butoxycarbonyl; and (a) R$^{12}$ and R$^{13}$ are taken separately and are each independently hydrogen, alkyl, phenyl, naphthyl, (C$_4$-C$_7$)cycloalkyl, adamantyl (C$_7$-C$_9$)phenylalkyl, (C$_{11}$-C$_{13}$)naphthylalkyl or (C$_5$-C$_{10}$) (cycloalkyl)alkyl, or R$^{12}$ is hydrogen and R$^{13}$ is

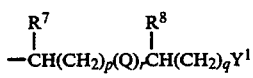

p, q, r and Q are as defined above;
$Y^1$ is methyl, phenyl, $-COOR^{18}$, $-CONR^9R^{10}$, $-CONHCOOCH_2C_6H_5$, $-NHCOCH_2C_6H_5$,

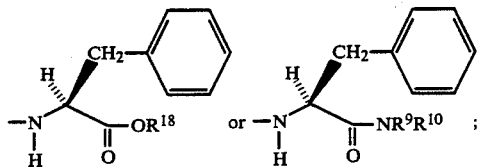

$R^7$, $R^8$, $R^9$ and $R^{10}$ are each independently as defined above; and
$R^{18}$ is an independent value of $R^7$ other than hydrogen; or (b) $R^{12}$ and $R^{13}$ are taken together with the nitrogen to which they are attached to form a pyrrole, indoline, isoindoline, piperidine, 1,2,3,4-tetrahydroquinoline, 1,2,3,4-tetrahydroisoquinoline, perhydroazepine, or morpholine ring system; and an intermediate compound of the formula

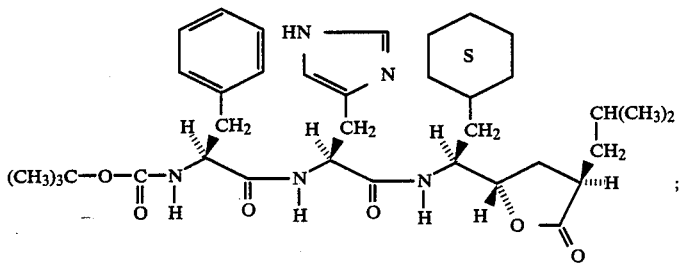

Finally, the present invention includes stereoselective processes as follows:

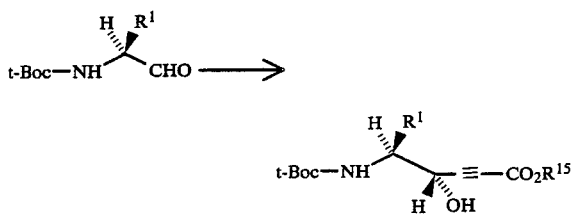

where $R^1$ is as defined above, but is other than hydrogen, and $R^{15}$ is ($C_1-C_3$)alkyl; and

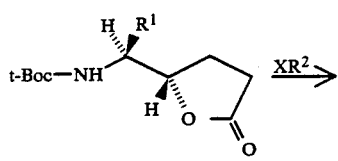

-continued where X is chloro, bromo or another nucleophilically displaceable group, $R^1$ and $R^2$ are as defined above, but $R^2$ is other than hydrogen and preferably an activating allyl or benzyl type group; and the resultant, pure, heretofore unavailable chiral intermediates of the formulae type (D), (E), (F), (G) and (H) below. The preferred value of X is bromo.

DETAILED DESCRIPTION OF THE INVENTION

The compounds of the invention are generally prepared by methods familiar to those skilled in the art. The basic sub-unit of the preferred chemical synthesis is the acylation of the unprotected alpha-amino group of an amino acid residue with an amino acid having an activated (for acylation purposes) carboxylic function and a suitable protecting group bonded to its own alpha-nitrogen to form a peptide bond between the two amino acid residues, followed by the removal of said protecting group. This synthesis sub-unit of coupling-deblocking is performed repeatedly to build up the polypeptide, starting from the C-terminal end of the molecular structure and working to the N-terminal end. The standard alpha-amino acids utilized to synthesize the compounds of the present invention are commercially available (as free acids, salts or esters, etc.) in both alpha-amino protected and alpha-amino unprotected forms Statine is commercially available as N-(t-butyloxycarbonyl)-statine; additionally, statine may be prepared (as a free acid or ester) in both the gamma-amino protected and gamma-amino unprotected forms by methods set forth in the literature [see e.g. U.S. Pat. No. 4,397,786 and Rich, D. H. et al., J. Org. Chem. vol. 43, pp. 3624 et seq. (1978). When desired, an appropriate N-unprotected amino acid analogue (free acid, salt or ester, etc.) such as 4-aminobutyric acid, 4-aminovaleric acid, 5-(benzyloxyoxycarbonylamino)pentylamine or ethyl 3-(2-aminoethoxy)propionate is used as a reactant in the first coupling step. If not commercially available or previously known, such compounds are readily prepared by methods well known in the art of organic chemistry When the desired product contains a basic amino acid residue $W^2$ (i.e. m=1), the required intermediate $H-(W^3)-NR^{12}R^{13}$ (wherein $W^3$, $R^{12}$ and $R^{13}$ are defined above) is prepared from lysine, ornithine or arginine, protected on the alpha-NH group with a hydrolyzable group such as t-butoxycarbonyl (t-Boc) which can be cleaved under anhydrous acid conditions e.g. ca. 3-5N HCl in dioxane, or anhydrous trifluoroacetic acid) and on omega-nitrogen with a hydrogenolyzable group such as benzyloxycarbonyl (cbz), by coupling with an amine $HNR^{12}R^{13}$. Preferred coupling conditions employ more or less equimolar quantities of the reagents to be coupled, dicyclohexylcarbodiimide (or a similar dehydrative coupling agent) in an equimolar quantity and 1-hydroxybenzotriazole in 1-2 molar quantity, in a reaction inert solvent such as $CH_2Cl_2$ at 0°-50° C. (conveniently at ambient temperature). When a reactant is in the form of an acid salt, a tertiary amine (e.g., triethylamine, N-methylmorpholine) is employed in an amount sufficient to neutralize said acid. Prior to the next coupling step the alpha-amino group of the basic amino acid residue $W^2$ is deprotected, e.g., an alpha-t-Boc group is readily removed by the action of 3.5 to 4.5N HCl in dioxane at −10° to 40° C., conveniently at ambient temperature; or by the action of anhydrous trifluoroacetic acid at −20° to 20° C., conveniently at about 0°-5° C.

The required 2,5-disubstituted-4-hydroxypentanoic acid residues must generally be synthesized. A present stereoselective route is from a precursor of appropriate chirality, conveniently an L-amino acid, e.g., in the initial stages:

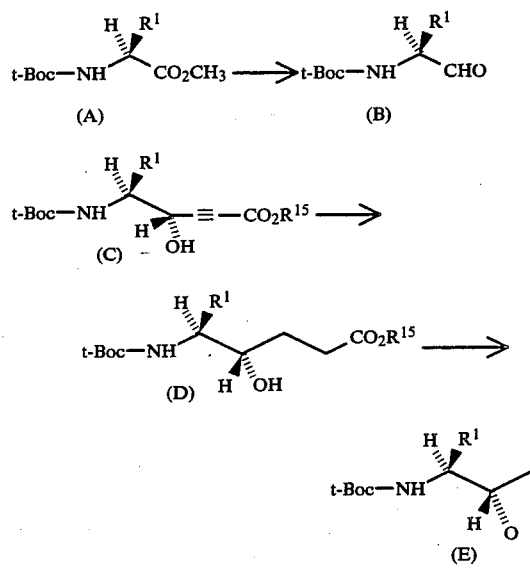

The starting protected L-amino acid is obtained commercially or by standard methods well known in the art, including, when desired, reduction of an aromatic ring, e.g., that of N-(t-butoxycarbonyl)phenylalanine methyl ester as exemplified below. The lower alkyl ester, preferably the methyl ester as shown is readily reduced to the aldehyde, for example, with diisobutylaluminum hydride in toluene at −50 to −80° C. The aldehyde in turn is reacted with $LiC≡CCOOR^{15}$ (usually $R^{15}$ is ethyl formed in situ from ethyl propiolate), again at −50° to −80° C., in a reaction inert solvent such as tetrahydrofuran. A pair of diastereoisomers are generally formed at this stage, with the desired diastereoisomer (C) greatly predominating. The lesser, undesired isomer is preferably removed following hydrogenation of the triple bond (carried out under standard hydrogenation conditions, e.g., over a palladium catalyst, preferably Pd in $BaSO_4$ under relatively mild conditions; and formation of the lactone (e.g., by reacting in toluene in the presence of acetic acid).

The desired lactone epimer, having the 4S stereochemistry shown in formula (E) and F), is then condensed with a halide, $R^2X$ (X=Cl, Br or I; preferably X=Br) in the presence of a substantial excess, e.g., 2 to 2.5 molar equivalents of a strong base of low nucleophilicity, such as $LiN[CH(CH_3)]_2$ or preferably, lithium hexamethyldisilazide. Preferably the halide is an allylic or benzylic type halide (e.g., 2-methyl-2-propenyl bromide, benzyl bromide) with the double bond or aromatic ring subsequently hydrogenated if the saturated group $R^2$ is desired, e.g.,

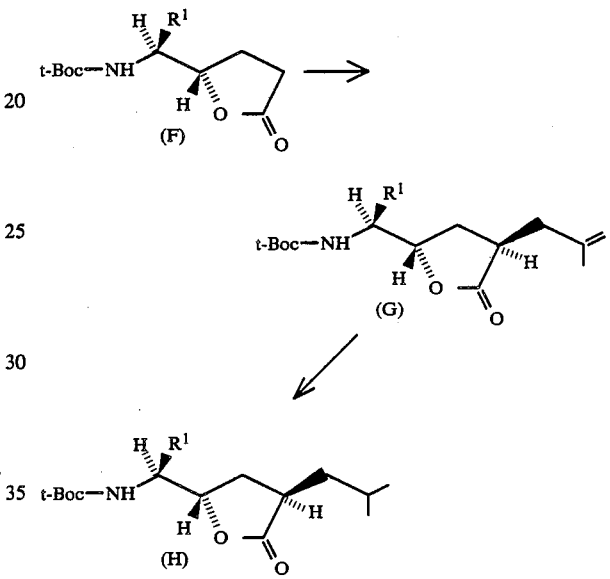

Once again, the desired diastereoisomer, having trans (2R) stereochemistry as shown, predominates It is separated by chromatography (before or after any required hydrogenation to produce the desired group $R^2$). Alternatively, hydrogenation, particularly when $R^2$ at the stage of condensation is a benzyl group, can be deferred until latter in the overall synthesis of the desired compound. The preferred catalysts for hydrogenation of a simple olefin comprise Pd or Rh, while for reduction of phenyl to cyclohexyl, Rh is preferred. In certain preferred embodiments of the present invention, particularly when $NR^{12}R^{13}$ is simple amine, such as $NH_2$, $NHCH_3$, $N(CH_3)_2$ or $NHCH_2C_6H_5$, the lactone is reacted directly with the appropriate amine, e.g.,

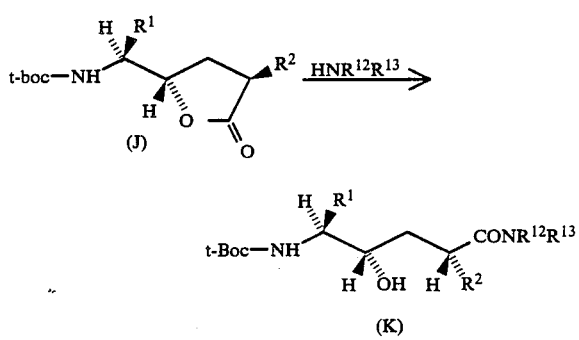

(II, m = O, R¹¹ = t-Boc)

The lactones react smoothly with excess of lower molecular weight, more basic amines such as $NH_3$, $NH_2CH_3$ and $NH(CH_3)_2$ at lower temperatures (e.g., 0° to 40° C.) in a reaction inert solvent. With more hindered or less basic amines, higher temperatures e.g., 80°–100° C., are employed, optionally in the presence of an acetic acid catalyst.

With more complex $NR^{12}R^{13}$ groups, it is preferred to convert lactone, via saponification of the blocked lactone (J) to acid with dilute NaOH in an aqueous solvent, conversion of the acid to benzyl ester using benzyl bromide in the presence of $K_2CO_3$ in a reaction inert solvent such as dimethylformamide, formation of tetrahydropyranyl ether by the action of 3,4-dihydro-2H-pyran in a reaction-inert solvent in the presence of a catalyst such as pyridinium p-tosylate and finally hydrogenolysis to the acid:

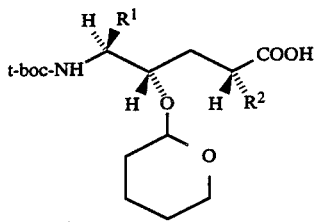

The latter is then coupled with an amino compound

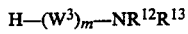

using the dehydrative coupling method (e.g., with dicyclohexylcarbodiimide) which is described above, or the so-called mixed anhydride procedure, also well known in the art and exemplified below; followed by selective hydrolysis of the tetrahydropyranyl ether by warming in aqueous acetic acid to produce the intermediate compound of the formula (II) wherein $R^{11}$ is t-butoxycarbonyl.

The compound of the formula (II) wherein $R^{11}$ is t-Boc, regardless of its source, is then selectively cleaved (by the methods described above) to yield the free amino compound (II) wherein $R^{11}$ is hydrogen.

In the final stages of the preferred process, the intermediate is coupled with

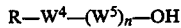

wherein R and n are as defined above; and $W^4$ and $W^5$ correspond to above W and $W^1$ respectively, but with imidazole nitrogen of any histidine residue blocked with t-butoxycarbonyl. The preferred coupling method employs dicyclohexylcarbodiimide using conditions as described above. This preferred method shows particular advantage, when n is 1, over the usual method of introducing each amino acid in single, sequential steps. Finally, any imidazole t-boc protecting group is selectively removed by hydrolysis in aqueous acetic acid (e.g., 80% acetic acid) at 10°–40° C., and any N-benzyloxycarbonyl or benzyl ester blocking groups are selectively removed by standard hydrogenation methods as described above, leaving the generally desired N-terminal protecting group intact.

The activity of the compounds of the present invention as inhibitors of the angiotensinogen-cleaving activity of renin is determined by studying (1) their ability to inhibit the angiotensinogen-cleaving activity of renin in vitro. In this test, blood plasma is obtained from healthy laboratory personnel, pooled and stored frozen until required. Before use, a quantity of this plasma is defrosted and centrifuged, and the supernatant mixed with protease inhibitors and buffered to pH 7.4. Renin inhibitors are added at different levels to different aliquots of the plasma supernatant, and the resulting mixtures (310 lambda) incubated for three hours at 37° C. along with renin inhibitor-free control mixtures. After incubation, the mixtures are quenched in ice water and each assayed for angiotensin I using angiotensin I antibody. The production of angiotensin I in the presence of a renin inhibitor is compared to that produced in the absence of the inhibitor, and a percentage inhibition is calculated. Using data obtained from duplicate incubations at each of several difference inhibitor concentrations, the inhibitor concentration in the incubation mixture required to produce a fifty percent inhibition of the angiotensinogen-cleaving activity of renin, i.e. the $IC_{50}$ of the inhibitor, is calculated for various different inhibitors. The angiotensin I in the quenched incubation mixtures is assayed by means of a radioimmunoassay, using components of a renin radioimmunoassay kit supplied by Becton Dickinson and Co. (Orangeburg, N.Y.). This radioimmunoassay was based upon the one developed by Haber et al., *J. Clin. Endocrinol.*, 29, pp. 1349–1355 (1969).

The activity of the present compounds may also be determined by their ability to antagonize the exogenous renin-induced pressor response in vivo. Male Sprague-Dawley rats (230 to 300 g. body weight) are anesthetized with sodium pentobarbital (65 mg./kg. body weight, intraperitoneal), after which femoral vein and carotid artery catheters are implanted in each animal Following completion of surgery, the animals are placed in the prone position and rectal temperature monitored continuously. Mean arterial blood pressure (MAP) is recorded via the carotid artery catheter using a Statham P23 ID pressure transducer and a physiograph. Subsequent to a stabilization period, control renin pressor responses (dP) of 20 to 30 mm Hg are obtained by administration of hog renin (30 to 80 mU/kg. body weight, intravenous), the animals are rechallenged with hog renin (same dosage as for control response) at 5, 15 and 30 minutes after renin inhibitor administration and the corresponding renin pressor responses (dP) measured. Percent antagonization is calculated as $$\frac{(\text{control } dP - \text{experimental } dP) \times 100\%}{\text{control } dP},$$

where control dP and experimental dP are the pressor changes in MAP before and after renin inhibitor administration, respectively. Preferably, at least three animals are used in each test, with results averaged The compounds of the present invention can be administered as antihypertensive agents by either the oral or parental routes of administration, and are routinely effective by the latter route, particularly when dosed as an intravenous solution. Where gastrointestinal adsorption permits, oral administration is preferred for reasons of patient convenience and comfort. In general, these antihypertensive compounds are normally administered in dosages ranging from about 0.1 mg. to about 10 mg. per kg. of body weight per day; variations will necessarily occur depending upon the condition of the subject being treated and the particular compound being administered. Typically, treatment is commenced at a low daily dosage and increased by the physician only if necessary. It is to be noted that these compounds may be administered in combination with pharmaceutically acceptable carriers by either of the routes previously indicated, and that such administration can be carried out in both single and multiple dosages.

For parenteral use, the present compounds are formulated according to the known art using suitable dispersing or wetting agents and suspending agents. The sterile injectable formulation can also be a solution of suspension in a non-toxic parenterally acceptable diluent or solvent, for example, as a solution in 1,3-butandiol. Among the acceptable vehicles and solvents are water, Ringer's solution and isotonic NaCl solution, fixed oils including synthetic mono- or diglycerides, fatty acids such as oleic acids, and mixtures thereof.

For oral administration, a wide variety of dosage forms are used, e.g., tablets, capsules, lozenges, troches, hard candies, powders, sprays, aqueous suspension, elixirs, syrups, and the like formulated with various pharmaceutically-acceptable inert carriers. Such carriers include solid diluents or fillers, sterile aqueous media and various non-toxic organic solvents, etc. In general, the compounds of this invention are present in such oral dosage forms at concentration levels ranging from about 0.5% to about 90% by weight of the total composition, in amounts which are sufficient to provide the desired unit dosage. Tablets may contain various excipients such as sodium citrate, calcium carbonate and calcium phosphate, along with various disintegrants such as starch (preferably potato or tapioca starch), alginic acid and certain complex silicates, together with binding agents such as polyvinylpyrrolidione, sucrose, gelatin and acacia. Additionally, lubricating agents such as magnesium stearate, sodium lauryl sulfate and talc are often very useful for tabletting purposes. Solid compositions of a similar type may also be employed as fillers in soft and hard-filled gelatin capsules; preferred materials in this connection would also include lactose or milk sugar as well as high molecular weight polyethylene glycols. When aqueous suspensions and/or elixirs are desired for oral administration, the essential active ingredient therein may be combined with various sweetening or flavoring agents, coloring matter or dyes and, if so desired, emulsifying and/or suspending agents as well, together with such diluents as water, ethanol, propylene glycol, glycerin and various like combinations thereof.

All structural designations of stereochemistry shown herein represent absolute stereochemistry. The present invention is illustrated by the following examples. However, it should be understood that the invention is not limited to the details of these examples. All temperatures are in °C. and are ambient unless otherwise specified. All stripping of solvents was in vacuo. All standard solutions are in water unless otherwise specified. THF stands for tetrahydrofuran; DMF stands for dimethylformamide; DME stands for 1,2-dimethoxyethane; and DMSO stands for dimethylsulfoxide. All standard alpha-amino acids or derivatives are in the L-form. Statine is 3S,4S-4-amino-3-hydroxy-6-methylheptanoic acid.

EXAMPLE 1

S-3-Cyclohexyl-2-(t-butoxycarbonylamino)-propionaldehyde

Methyl S-3-cyclohexyl-2-(t-butoxycarbonylamino)-propionate (51.2 g., 0.179 mol) was dissolved in 728 ml. of dry toluene and cooled to −78°. Diisobutylaluminum hydride (449 ml. of 1M in toluene, 0.449 mol) was added dropwise over 1 hour, maintaining −70° to −78°. Methanol (13 ml.) was added at −70°, followed by 608 ml. of half-saturated sodium potassium tartrate, and the mixture warmed to ambient temperature. Ether (300 ml.) was added and the organic layer was separated and washed with 1 l. saturated sodium potassium tartrate. The original aqueous layer was extracted with 600 ml. fresh ether and backwashed with 600 ml. fresh saturated sodium potassium tartrate. The organic layers were combined, dried over $MgSO_4$ and stripped to yield title product as a gum, contaminated with toluene on the basis of $^1$H-nmr, 45.6 g; tlc Rf 0.45 (1:3 ethyl acetate:-hexane); $^1$H-nmr ($CDCL_{13}$) delta: 0.9 to 2.3 (m), which includes t-butyl singlet at 1.4, 3.0–4.8 (m), 4.9–5.2 (d), 9.6 s).

EXAMPLE 2

Ethyl 4RS,5S-6-Cyclohexyl-5-(t-butoxycarbonylamino)-4-hydroxy-2-hexynoate

Dry freshly distilled THF (117 mol) and diisopropylamine (22.0 ml., 15.8 g., 0.156 ml.) were charged to a flame dried reaction flask under $N_2$ and the resulting solution cooled to −30° and butyllithium (76.9 ml. of 1.6M in hexane, 0.123 mol) added over 5 minutes. The solution was then cooled to −78° and ethyl propiolate 12.5 ml., 12.1 g., 0.123 mol) added dropwise over 20 minutes, maintaining the temperature −65° to −78°. After 30 minutes at −78°, title product of the preceding Example (19.52 g., 0.0866 mol) in 35 ml. THF was added over 20 minutes, again maintaining −65° to −78°. After 2 hours, 200 ml. of 5 1 THF:acetic acid was added to the reaction mixture, and it was allowed to warm to ambient temperature and diluted with a half volume of ether and an equal volume of 10% citric acid.

The organic layer was separated, washed sequentially with 2×200 ml. fresh 10% citric acid, 200 ml of brine and 2×200 ml saturated $NaHCO_3$, dried over $MgSO_4$ and stripped to a dark red oil, 38.2 g. The latter was chromatographed on a 10 cm×42 cm column of silica gel with tlc monitoring, eluting with 5 1. of 1:9 ethyl acetate:hexane. After 1500 ml. to develop the column, 500 ml. fractions were collected. Fractions 29–37 were combined and stripped to yield title product as an oil, 15.3 g.; tlc Rf 0.44 (3:7 ethyl acetate:hexane); $^1$H-nmr ($CDCl_3$) delta: 1.0–2.0 (m, 25H) including singlet for the t-butyl group at 1.5, 3.8–5 (m, 6H).

EXAMPLE 3

4S,5S-6-Cyclohexyl-5-(t-butyloxycarbonylamino)-gamma-hexanolactone

Title product of the preceding Example (18.28 g.) and 5% $Pd/BaSO_4$ (10.97 g.) were combined with 150 ml. ethyl acetate and hydrogenated for 2 hours under 4 atmospheres pressure of hydrogen. The catalyst was recovered by filtration and the filtrate stripped to yield intermediate ethyl 4RS,5S-6-cyclohexyl-4-hydroxy5-(t-butyloxyamino)hexanoate, 19 g. The latter was taken up in 250 ml. of 2.5% acetic acid in toluene, refluxed 2.5 to 3 hours, stripped and the residue chromatographed on a 10 cm.×30 cm. column of silica gel, monitoring by tlc, eluting with 4 l of 9:11 ether:hexane, 8 l. of 1:1 ether:hexane, 2 l. of 11:9 ether:hexane and finally 3 l. of 3:2 ether:hexane, collecting 28×400 ml. fractions, 6×150 ml. fractions and finally 11×400 ml. fractions Fractions 17-24. were combined and co-stripped with ether to yield the predominant and desired, less polar, 4S,5S-title product as an oil, 9.13 g.; tlc Rf 0.5 (7:3 ether hexane). The more polar, 4R,5S-epimer of title product was isolated by stripping combined fractions 28-45 and crystallized by trituration with hexane, 1.77 g.; mp 101.5°-103.5°.

EXAMPLE 4

2R,4S,5S- and 2S,4S,5S-6-Cyclohexyl-5-(t-butoxycarbonylamino)-2-(2-methyl-2-propenyl)-gamma-hexanolactone Dry freshly distilled THF (30 ml.) and diisopropylamine (3.51 ml., 2.52 g., 0.0249 mol) were charged to a flame dried reaction flask under $N_2$, the resulting solution was cooled to −50°, butyllithium (13.9 ml. of 1.6M in hexane, 0.0222 mol) was added and the mixture further cooled to −78°. Title product of the preceding Example (2.77 g., 0.0089 mol) in 15 ml. THF was added dropwise over 10 minutes and the enolate allowed to form over a further 20 minutes at −78°, at which time 3-bromo-2-methyl-1-propene in 5 ml. THF was added over 10 minutes, and the mixture stirred an additional 1 hour at −78°, quenched with 5 ml. saturated $NH_4Cl$, warmed to room temperature, diluted with a half volume of ether, washed 2×50 ml. 10% citric acid, 2×50 ml. saturated $NaHCO_3$ and 1×25 ml. brine, dried over $MgSO_4$ and stripped to an oil, 3.06 g., a mixture of the title epimers. The latter were separated by chromatography on 7 cm×20 cm silica gel; monitoring by tlc; eluting sequentially with 2 l. of 1:9 ether:hexane, 4 l. of 3:17 ether:hexane, 2 l. of 1:4 ether:hexane, 2 l. of 1:3 ether:hexane, 2 l. of 7:13 ether:hexane and 2 l. of 1:1 ether hexane; and collecting 125 ml. fractions. The less polar title product, having trans (2R) stereochemistry, was collected in fractions 30-48, combined and stripped to yield same as an oil, 1.17 g.; tlc Rf 0.45, (2:3 ether:hexane); $^1$H-nmr ($CDCl_3$) delta 1.4 (s, 9H), 1.8 (s, 3H), 0.3-3.0 (m, 18H), 3.6-4.0 (m, 1H), 4.69 (s, 1H), 4.75 (s, 1H), 4.1-4.8 (m, 2H). Fractions 55-76 gave the more polar title product, also as an oil, 0.358 g., having cis (2S) stereochemistry; tlc Rf 0.36 (2:3 ether:hexane); $^1$H-nmr identical to that of the less polar epimer.

EXAMPLE 5

2R,4S,5S- and 2S,4S,5S-6-Cyclohexyl-5-(t-butoxycarbonylamino)-2-(2-methylpropyl)-gamma-hexanolactone The less polar title product of the preceding Example (1.17 g.) and 10% Pd/C (0.351 g.) were combined in 20 ml. ethyl acetate and hydrogenated at 4 atmospheres pressure for 2.5 hours, the catalyst recovered by filtration and the filtrate stripped to yield less polar title product (likewise having trans, i.e., 2R stereochemistry) as an oil which crystallized on standing, 1.20 g.; mp 88°-93°; tlc Rf 0.65 (1:1 ether: hexane), Rf 0.73 (2:1 ethyl acetate:hexane). The other isomer, having cis (2S) stereochemistry, was obtained in like manner; tlc Rf 0.59 (1:1 ether:hexane). In subsequent Examples, which employ the present less polar epimer of Rf 0.65 (1:1 ether:hexane), 2R stereochemistry is specified.

EXAMPLE 6

Benzyl 2R,4S,5S-6-Cyclohexyl-5-(t-butoxycarbonylamino) 4-hydroxy-2-(2-methylpropyl)hexanoate The less polar 2R title product of the preceding Example (1.0 g., 2.72 mmols), DME 14 ml.) and NaOH (4.4 ml. of 5N, 0.022 mol) were combined, stirred for 12 hours and then stripped of organic solvent. The aqueous residue was diluted with water (5 ml.), layered with an equal volume of ether, cooled to 0° and acidified with 22 ml. of 1N HCl, by which time the aqueous layer was turbid. The ether layer was separated and the aqueous layer (pH 2.0) washed with an equal volume of fresh ether. The ether layers were combined, dried over $MgSO_4$ and stripped to yield intermediate 2R,4S,5S-6-cyclohexyl-5-(t-butoxycarbonylamino)-4-hydroxy-2-(2-methylpropyl)hexanoic acid as a white foam, 0.909 g. (2.36 mmols). The latter was charged into 20 ml. DMF together with $K_2CO_3$ (0.330 g., 2.36 mmols) and cooled to 0°. Benzyl bromide (0.308 ml., 0.443 g., 2.59 mmols) was added and the stirred mixture allowed to warm to room temperature. After 4 hours, the reaction mixture was diluted with an equal volume of ether, washed 1×75 ml. 10% citric acid, 1×75 ml. saturated $NaHCO_3$, dried over $MgSO_4$, and stripped to yield an oil, 1.35 g. The latter was chromatographed on 4 cm×20 cm silica gel; monitored by tlc; eluting with 1 l. 1:9 ether hexane, 1 l. 3:17 ether: hexane, 1 l. 1:4 ether hexane and finally 1 l. 3:7 ether:hexane; and collecting 23 ml. fractions. Fractions 46-75 were combined and stripped to yield crystalline starting material, 0.583 g., suitable for recycling. Fractions 85-119 were combined and stripped to yield present title product as an oil, 0.275 g.; tlc Rf 0.47 (1:1 ether:hexane); $^1$H-nmr (CDCl): 0.3-2.0 (m, 24H), 1.4 (s, 9H), 2-2.4 (m, 1H), 2.6-3.0 (m, 1H), 3.2-3.7 (m, 2H), 4.65 (d, 1H), 5.1 (s, 2H), 7.3 (s, 5H).

EXAMPLE 7

Benzyl 2R,4S,5S-6-Cyclohexyl-5-t-butoxy-carbonylamino)-2-(2-methylpropyl)-4-(2-tetrahydropyranyloxy)hexanoate The product of the preceding Example (0.442 g., 0.929 mmol), 3,4-dihydro-2H-pyran (97%, 0.255 ml., 0.235 g., 2.79 mmols) and pyridinium p-tosylate (23 mg., 0.093 mmol) were combined in 6.5 ml. $CH_2Cl_2$ and stirred in a stoppered flask for 18 hours, then stripped of solvent and the residue taken up in 100 ml. ether, washed 2×100 ml. half saturated brine, dried over $MgSO_4$, co-stripped with $CH_2Cl_2$, and dried under high vacuum to yield present title product as an oil, 0.565 g.; tlc Rf 0.59 (2:3 ether:hexane).

EXAMPLE 8

2R,4S,5S-6-Cyclohexyl-5-(t-butoxycarbonylamino)-2-(2-methylpropyl)-4-(2-tetrahydropyranyloxy)hexanoic Acid The product of the preceding Example (0.565 g.) and 10% Pd/C (0.170 g.) were combined in 10 ml. ethyl acetate and hydrogenated at 4 atmospheres pressure for 2.5 hours. The catalyst was recovered by filtration and the filtrate co-stripped with $CH_2Cl_2$ to yield title product as an oil, 0.55 g., which contains the theoretical yield (0.474 g.) of product; tlc Rf 0.0 (2:3 ether:hexane), 0.35 (1:1 ethyl acetate:hexane); $^1$H-nmr (CDCl$_3$) includes 9.5-10.1 (bs, 1H, COO$\underline{H}$) and no peaks due to a benzyl group.

This example was repeated on a 300 mg. scale with drying of the product under high vacuum to produce 250.5 mg. (a quantitative yield of title product as a white foam).

EXAMPLE 9

N-[N-alpha-(t-Butoxycarbonyl)-N-epsilon(benzyloxycarbonyl) lysyl]phenylalanine Benzyl Ester N-hydroxybenzotriazole (162 mg., 1.2 mmoles), N-methylmorpholine (101.2 mg., 1 mmole), L-phenylalanine benzyl ester p-toluenesulfonate (428 mg., 1 mmole), N-alpha-(t-butyloxycarbonyl)-N-epsilon-benzyloxycarbonyl-L-lysine (456 mg., 1.2 mmoles) and 1-cyclohexyl-3-(2-morpholinoethyl)carbodiimide metho-p-toluene sulfonate (635 mg, 80% pure, 1.2 mmoles) were sequentially dissolved in methylene chloride (50 ml.) at 0° C., and the resulting solution stirred for 19 hours at 20° C. The reaction mixture was then washed consecutively with 75 ml. of 5.5% aqueous HCl, 75 ml. of saturated aqueous NaHCO$_3$ and 75 ml. of brine, dried over MgSO$_4$, and stripped to yield title product as a dry foam, 0.669 g.; $^1$H-nmr (CDCl$_3$) includes delta 1.5 (s, 9H, t-butyl). The product was used directly in the next Example, without further purification.

EXAMPLE 10

N-[N-epsilon-(Benzyloxycarbonyl)lysyl]phenylalanine Benzyl Ester Hydrochloride

Product of the preceding step (0.650 g.) was dissolved in 7 ml. of 3.7N HCl in dioxane, allowed to stand 1 hour, and stripped to yield title product, 0.583 g.; $^1$H-nmr (CD$_3$OD) includes delta 5.2 (s, 2H, —C$\underline{H}_2$C$_6$H$_5$).

EXAMPLE 11

N-(N-alpha-[2R,4S,5S-6-Cyclohexyl-5-(t-butoxycarbonylamino)-4-hydroxy-2-(2-methylpropyl)hexanoyl]-N-epsilon-(benzyloxycarbonyl) lysyl))-phenylalanine Benzyl Ester Hydrochloride The product of the preceding Example (0.560 g., 1.01 mmols) was stirred with 5 ml. CH$_2$Cl$_2$ and cooled to 0° under nitrogen. Triethylamine (0.211 ml., 1.51 mmols) and then the product of Example 8 (0.474 g., 1.01 mmols) in 5 ml. CH$_2$Cl$_2$ were added. Finally, 1-hydroxybenzotriazole (0.204 g., 1.51 mmoles) and then dicyclohexylcarbodiimide (0.208 g., 1.01 mmols) in 5 ml. CH$_2$Cl$_2$ were added. The reaction mixture was allowed to warm to ambient temperature and stirred 18 hours. The resulting suspension was filtered and the filtrate stripped of CH$_2$Cl$_2$ diluted with 15 ml. ethyl acetate, and refiltered. The second filtrate was washed 2×10 ml. 10% citric acid, 2×10 ml. saturated NaHCO$_3$ and 1×10 ml. brine, dried over MgSO$_4$ and co-stripped with CH$_2$Cl$_2$ to yield intermediate tetrahydro-2-pyranyl ether of title product, 0.97 g. The latter was stirred for 20 hours with 35 ml. 70% acetic acid. The mixture was stripped to low volume and the residue co-stripped with toluene to produce a solid, white residue. The latter was taken into 20 ml. CH$_2$Cl$_2$, washed 1×10 ml. brine and 2×10 ml. saturated NaHCO$_3$, dried over MgSO$_4$, and stripped to yield white solids, 1.02 g., which were chromatographed on 7 cm×15 cm silica gel eluting with 2 1. 0.5% methanol in CHCl$_3$, monitoring by tlc and collecting 125 ml fractions. Title product was recovered as a white solid by stripping combined fractions 29-40 and triturating the residue with ether, 0.497 g.; mp 157°-159° ; tlc Rf 0.39 (1:1 ethyl acetate:hexane); $^1$H-nmr (CDCl$_3$) includes 1.4 (s, 9H, t-butyl) and 6.5-7.4 (m, 15H, aromatic).

EXAMPLE 12

N-alpha-((2R,4S,5S-6-Cyclohexyl-5-[(N-t-butoxycarbonylphenylalanyl) histidyl]amino-4-hydroxy-2-[2-methylpropyl)hexanoyl))-N-epsilon-(benzyloxycarbonyl)) lysyl-phenylalanine Benzyl Ester Product of the preceding Example (250 mg., 0.282 mmol) was stirred with 3 ml. trifluoroacetic acid, protected from moisture by a CaCl$_2$ drying tube, and cooled to 0°. After 35 minutes the reaction was co-stripped with ether to yield intermediate N-((N-alpha-[2R,4S,5S-6-cyclohexyl-5-amino-4-hydroxy-2-(2-methylpropyl)hexanoyl]-N-epsilon-(benzyloxycarbonyl)lysyl))phenylalanine benzyl ester trifluoroacetate salt as a white foam, 0.291 g. The latter, under N$_2$ was taken into 2 ml. CH$_2$Cl$_2$, cooled to 0° and triethylamine (0.0471 ml., 0.0342 g., 0.338 mmol), 1-hydroxybenzotriazole (0.0571 g., 0.423 mmol), N-alpha-[N-(t-butoxycarbonyl)phenylalanyl]-N(imidazole)-(t-butoxycarbonyl) histidine (149.7 mg., 0.296 mmol) and dicyclohexylcarbodiimide (61.1 mg., 0.296 mmol) in 5 ml. CH$_2$Cl$_2$ were added sequentially. The reaction mixture was allowed to warm to room temperature, stirred for 18 hours, the resulting suspension stripped of solvent, the residue suspended in 5 ml. ethyl acetate, filtered to removed dicyclohexyl urea, yielding 373 mg. of solids, determined by tlc to also contain considerable amounts of the desired intermediate product retaining the histidine imidazole-(tbutoxycarbonyl) protecting group on gamma histidine nitrogen; tlc Rf 0.51 (1:19 methanol:CHCl$_3$). The filtrate was stripped to 140 mg. residue containing additional intermediate by tlc and $^1$H-nmr (CDCl$_3$) showing two singlets at 1.3 and 1.6 for the two t-butyl groups and a singlet at 5.1 for the methylene of the benzyl group. Both intermediate containing materials were combined and treated, with stirring under nitrogen, with 70 ml. of saturated dimethylamine in CHCl$_3$ for 3 hours. The reaction mixture was then stripped to solids free of amine odor, and chromatographed on 7 cm×15 cm of silica gel, gradiently eluting with 2 to 5% methanol in CHCl$_3$ and monitoring by tlc. Product fractions were combined, stripped and triturated with hexane/ether to yield title product as a white solid, 0.182 g.; tlc Rf 0.85 (1:1:1:1 ethyl acetate:butanol: acetic acid:H$_2$O), Rf 0.24 (1:19 methanol:CHCl$_3$); $^1$H-nmr (CDCl$_3$ with minor portion of CH$_3$OD) included 1.3 (s, 9H, t-butyl), 6.8 (s, 1H) and 7.5 (s, 1H)-imidazole protons, and 5.0 (s, 2H, C$\underline{H}_2$C$_6$H$_5$).

EXAMPLE 13

N-alpha-((2R,4S,5S-6-Cyclohexyl-5-[N-(t-butoxycarbonylphenylalanyl) histidyl]amino-4-hydroxy-2-(2-methylpropyl)hexanoyl))lysyl-phenylalanine Diacetate Product of the preceding Example (70 mg.) and 10% Pd/C (70 mg.) were combined with 10 ml. 4:1 methanol: acetic acid and hydrogenated at 4 atmospheres for 2 hours. The catalyst was recovered by filtration and the filtrate co-stripped with toluene to yield title product as a white powder, 73 mg.; tlc Rf 0.63 (1:1:1:1 ethyl acetate:butanol:acetic acid:H₂), Rf 0.0 (1:19 methanol:CHCl₃); ¹H-nmr (DMSO-d₆) includes 1.3 (s, 9H, t-butyl), no benzyl CH₂ protons and aromatic protons at 6.8–7.8 ppm; mp, decompose above 200°.

EXAMPLE 14

2R,4S,5S-6-Cyclohexyl-5-t-butoxycarbonylamino)-4-hydroxy-2-(2-methylpropyl)-N-methylhexanamide (Method A)

2R,4S,5S-6-Cyclohexyl-5-(t-butoxycarbonylamino)-2-(2-methylpropyl)-gamma-hexanolactone (197 mg., 0.536 mmol, Example 5) was dissolved in 1 ml. of water and cooled in an ice-water bath. The cold solution was perfused with CH₃NH₂ for 3 minutes, stoppered and allowed to stand at room temperature for 2 hours, by which time tlc indicated reaction was complete. The mixture was stripped of solvent and dried under high vacuum to yield title product as a white, solid foam, 204 mg.; tlc Rf 0.31 (3:1 ethyl acetate hexane).

EXAMPLE 15

2R,4S,5S-6-Cyclohexyl-5-amino-4-hydroxy-2-(2-methylpropyl)-N-methylhexanamide Hydrochloride Title product of the preceding Example (199 mg., 0.499 mmol) was dissolved in 4N HCl in dioxane (1 ml.) and stirred for 25 minutes under N₂, by which time tlc indicated complete consumption of starting material. The reaction mixture was then stripped of solvent and dried in high vacuum to produce title product as an incompletely dry, pale yellow powder, 185 mg.; tlc Rf 0.20 (18:2:1 CHCl₃:ethanol:acetic acid; the tlc plate was exposed to NH₃ vapor prior to elution to convert the HCl salt to free base)

EXAMPLE 16

2R,4S,5S-6-Cyclohexyl-5-[N-(N-(t-butoxycarbonyl)-phenylalanyl)norleucyl]amino-4-hydroxy-2-(2-methylpropyl)-N-methylhexanamide Title product of the preceding Example (61.8 mg., 0.185 mmol), CH₂Cl₂ (0.5 ml.), triethylamine (0.033 ml., 0.240 mmol), [N-(t-butoxycarbonyl)phenylalanyl]norleucine (70 mg., 0.185 mmol), 1-hydroxybenzotriazole (43 mg., 0.278 mmol) and dicyclohexylcarbodiimide (38 mg., 0.185 mmol) were added in sequence to a 2 ml. flask, the mixture stirred 18 hours at 0°, and the mixture filtered. The filtrate was diluted with 2.5 ml. CH₂Cl₂, washed 2×3 ml. 1N NaOH, 1×3 ml. brine, dried (MgSO₄) and stripped to an off white powder. The latter was chromatographed on 2 g. silica gel and gradiently eluted with 50 ml. each 0.5%, 1%, 2%, 4% and 6% ethanol in CH₂Cl₂ to yield 21.1 mg. of white powder contaminated with dicyclohexylurea (DCU). The latter was combined with the product and DCU containing solids which were initially isolated from the reaction mixture and chromatographed on 15 g. silica gel gradiently eluted with 500 ml. each 1%, 2%, 3% and 4% ethanol in CH₂Cl₂. Product fractions, free of DCU, were combined and stripped to yield title product, 60.4 mg.; ¹H-nmr (DMSO-d₆) 300 mHz (ppm) includes 0.9-0.95 (m, 9H, C(CH₃)₂ and C—CH₃); 1.33 (s, 9H, boc); 2.56 (d, 3H, NCH₃, J=ca 5Hz); 3.8, 4.18, and 4.32 m, 1H, each); 4.62 (d, 1H, J=ca.4Hz); 7.06, 7.46 and 7.95 (d, 1H each, J=ca.8Hz); 7.68 (q, 1H, J=ca 0.5Hz); 7.2–7.4 (m, aromatic).

EXAMPLE 17

2R,4S,5S-6-Cyclohexyl-5-(t-butoxycarbonylamino)-4-(2-tetrahydropyranyloxy-2-(2-methylpropyl)-N-methylhexanamide Title product of Example 8 (211 mg., 0.449 mmol) was dissolved in 1 ml. dry THF and cooled to −50° under N₂. With stirring, N-methylmorpholine (0.0545 ml., 0.494 mmol) was added and after 2-3 minutes, isobutylchloroformate (0.0641 ml., 0.494 mmol) was added dropwise. After an additional 10 minutes at −50°, the temperature was increased to −30° and methylamine (37.6 mg., 1.21 mmol) in 0.068 ml. of THF added dropwise over 20 minutes. After 10 minutes, the mixture was warmed to ambient temperature, diluted with 5 ml. of ethyl acetate, washed 3×5 ml. saturated NaHCO and then 1×5 ml. H₂O, dried (MgSO₄) and stripped to an oil, 245 mg. The latter was chromatographed on 5 g. silica gel eluting with 1:1 ether:hexane and monitoring by tlc to yield title product as a white solid foam, 102.2 mg.; tlc Rf 0.2 and 0.25 (3:1 ether:hexane), reflecting 1:1 epimers in the tetrahydropyranyl ether side chain.

EXAMPLE 18

2R,4S,5S-6-Cyclohexyl-5-(t-butoxycarbonylamino)-4-hydroxy-2-(2-methylpropyl)-N-methylhexanamide (Method B)

Title product of the preceding Example (98.6 mg., 0.204 mmol) was dissolved in 1.5 ml. of 2:1 acetic acid:-H₂O and stirred for 6 hours, then stripped and chased 2×CH₃C₆H₅ to yield an oil, 99.2 mg. The latter was chromatographed on 5 g. silica gel eluting with 200 ml. 1:1, then 100 ml. 3:1 ethyl acetate:hexane, monitoring by tlc. Clean product fractions were combined and stripped to yield title product as a white solid foam, 61.5 mg.; tlc Rf 0.22 (2:1 ethyl acetate:hexane); ¹H-nmr (CDCl₃) 300 mHz (ppm) includes 0.9 (d, 6H), 1.46 (s, 9H), 2.82 (d, 3H); identical with title product of Example 14.

By the method of Example 15, the present product (59.2 mg.) was converted to 2R,4S,5S-6-Cyclohexyl-5-amino-4-hydroxy-2-(2-methylpropyl)-N-methylhexaneamide hydrochloride, 50.0 mg., identical with the product of that Example.

EXAMPLE 19

2R,4S,5S-6-Cyclohexyl-5-[N-alpha-(N-t-butoxycarbonyl-phenylalanyl)-N(imidazol)-(t-butoxycarbonyl) histidyl]amino-4-hydroxy-2-(2-methylpropyl)-N-methylhexanamide By the method of Example 16, title product of Example 15 (47.3 mg., 0.141 mmol; prepared according to the immediately preceding Examples) and N-alpha-[N-(t-butoxycarbonyl)phenylalanyl]-N(imidazole)-(t-butoxycarbonyl)histidine (74.4 mg., 0.148 mmol) in 1 ml. CH₂Cl₂ were converted to instant title product. Following filtration of the reaction mixture, the filtrate was stripped of CH₂Cl₂ and diluted with 1 ml. ethyl acetate, washed 2×1 ml. 1N NaOH, 1×1 ml. brine, dried (MgSO₄) and stripped to a foam 123.6 mg., which was chromatographed on 4 g. silica gel, eluting with 100 ml. each 0.5%, 1%, 2%, 4% and 6% ethanol in CH₂Cl₂ and monitoring by tlc. Clean product fractions were combined and stripped to yield title product as a white solid foam, 84.4 mg.; tlc Rf 0.58 (18:2:1 CHCl₃:ethanol acetic acid).

EXAMPLE 20

2R,4S,5S-6-Cyclohexyl-5-[N-alpha-(N-t-butoxycarbonylphenylalanyl) histidyl]amino-4-hydroxy-2-(2-methylpropyl)-N-methylhexanamide Title product of the preceding Example (81.1 mg., 0.104 mmol) was dissolved in 1 ml. methanol and stirred under $N_2$ with about 5 mg. of $K_2CO_3$ for 1 hour. The $K_2CO_3$ was neutralized with acetic acid and the mixture stripped to near dryness, diluted with water and desalted on ion exchange resin (5 g. RP C-18) eluting with 2× column volume of 2:3 methanol:$H_2O$ and then 4× column volume of methanol. The non-aqueous fractions were combined, stripped and dried under high vacuum to yield title product as a white powder, 63.5 mg.; tlc Rf 0.03 (18:2:1 CHCl₃:ethanol:acetic acid); $^1$H-nmr (DMSO-$d_6$) 300 mHz (ppm) includes: 0.90 and 0.95 (doublets, 6H total, J=7Hz, C(CH₃)₂); 1.30 (s, 9H, C(CH₃)₃; 2.56 (d, 3H, J=ca. 5Hz, NCH₃); 3.72 (m, 1H); 4.14 (m, 1H); 4.47 (m, 1H); 7.53 (s, 1H, one imidazolyl CH); 6.86, 7.12, 7.76 and 8.22 m, 1H each, NH); 7.16-7.40 (m, aromatic).

EXAMPLE 21

2-[2R,4S,5S-6-Cyclohexyl-5-(t-butoxycarbonylamino)-4-(2-tetrahydropyranyloxy)-2-(2-methylpropyl) hexanoyl]-1,2,3,4-tetrahydroisoquinoline Title product of Example 8 (0.243 g., 0.517 mmol), tetrahydroisoquinoline (0.044 ml., 0.069 g., 0.517 mmol) and 1-hydroxybenzotriazole (70 mg., 0.517 mmol) were combined with 5 ml. $CH_2Cl_2$ and cooled to 0°. Dicyclohexylcarbodiimide (107 mg., 0.517 mmol) was added and the mixture stirred 18 hours at room temperature, filtered, the filtrate stripped and the residue triturated with 5 ml. ethyl acetate and refiltered. The second filtrate was washed 1×5 ml. 5% HCl, 1×5 ml. saturated NaHCO₃ and 1×5 ml. brine, dried (MgSO₄), stripped and the second residue chromatographed on 36 g. silica gel using 1% methanol in CHCl₃ as eluant, 229 mg.; $^1$H-nmr (CDCl₃) includes delta 1.4 ppm. (s, 9H, C(CH₃)₃).

EXAMPLE 22

2-[2R,4S,5S-6-Cyclohexyl-5-amino-4-hydroxy-2-(2-methylpropyl)hexanoyl]-1,2,3,4-tetrahydroisoquinoline Hydrochloride By the method of Example 15, the product of the preceding Example (176 mg., 0.301 mmol) was converted to incompletely dry, title product, 153 mg.; $^1$H-nmr (CD₃OD) includes delta 1.2 ppm (6H, J=7, —CH(CH₃)₂).

EXAMPLE 23

2-[2R,4S,5S-6-Cyclohexyl-5-N-alpha-N-t-butoxycarbonylalanyl)-N (imidazole)-(t-butoxycarbonyl) histidyl)amino-4-hydroxy-2-(2-methylpropyl)hexanoyl]-1,2,3,4-tetrahydroisoquinoline By the method of Example 16, using N-methylmorpholine in place of triethylamine, the wet product of the preceding Example (153 mg., 0.301 mmol assumed) and N-alpha-(N-t-butoxycarbonylphenylalanyl)-N(imidazole)-(t-butoxycarbonyl) histidine (186 mg., 0.367 mmol) were converted to instant title product. The reaction mixture was filtered and the filtrate chromatographed on silica gel using 2.5% methanol in CHCl₃ as eluant to yield present title product, 286 mg.; $^1$H-nmr (CDCl₃) includes delta 1.4 ppm (s, 9H, C(CH₃)₃).

EXAMPLE 24

2-[2R,4S,5S-Cyclohexyl-5-(N-(N-t-butoxycarbonylphenylalanyl) histidyl)amino-4-hydroxy-2-(2-methylpropyl)hexanoyl]-1,2,3,4-tetrahydroisoquinoline Title product of the preceding Example (286 mg.) was stirred for 6 days with 10 ml. 4:1 acetic acid:$H_2O$, then stripped with toluene chase and the residue chromatographed on 20 g. silica gel with 10% methanol in CHCl₃ as eluant to yield title product, the less polar of 2 products, 110 mg.; $^1$H-nmr (CDCl₃) includes 1.4 ppm (s, 9H, C(CH₃)₃).

EXAMPLE 25

N-[2R,4S,5S-6-Cyclohexyl-5-(t-butoxycarbonylamino)-4-(2-tetrahydropyranyloxy)-2-(2-methylpropyl) hexanoyl]proline Methyl Ester Except to use a reaction time of 2 hours at 0° and 16 hours at room temperature, to use N-methylmorpholine in place of triethylamine, and to use 1% methanol in CHCl₃ as eluant on chromatography, the method of Example 19 was employed to convert the product of Example 8 (300 mg., 0.639 mmol) and proline methyl ester hydrochloride (106 mg.; 0.639 mmol) to title product, 215 mg.; $^1$H-nmr (CDCl₃) includes delta 1.4 ppm (s, 9H, C(CH₃)₃); tlc Rf 0.7 (2.5% CH₃OH in CHCl₃).

EXAMPLE 26

N-[2R,4S,5S-6-Cyclohexyl-5-(t-butoxycarbonylamino)-4-hydroxy-2-(2-methylpropyl)hexanoyl]-proline Methyl Ester Product of the preceding Example (165 mg.) was stirred in 10 ml. 4:1 acetic acid:$H_2O$ for 18 hours, stripped, and chased 2×5 ml. toluene and 1×5 ml. CHCl₃ to yield somewhat wet title product as an oil, 166 mg.; tlc Rf 0.6 (2.5% CH₃OH in CHCl₃).

EXAMPLE 27

N-[2R,4S,5S-6-Cyclohexyl-5-amino-4-hydroxy-2-(2-methylpropyl)hexanoyl]proline Methyl Ester Title product of the preceding Example (166 mg., wet) was combined with 3.7N HCl in dioxane (1 ml.). After 2 hours, the mixture was stripped, taken up in 5 ml ethyl acetate, washed 1×5 ml. saturated NaHCO₃ and then 1×5 ml. brine, dried (MgSO₄) and restripped to yield title product, $^1$H-nmr (CD₃OD) includes delta 3.8 ppm (s, 3H, CO₂CH₃).

EXAMPLE 28

N-[2R,4S,5S-6-Cyclohexyl-5-(N-alpha-(N-t-butoxycarbonylphenylalanyl)-N (imidazole)-(t-butoxycarbonyl) histidyl)amino-4-hydroxy-2-(2-methylpropyl)hexanoyl]proline Methyl Ester The product of the preceding Example (132 mg., 0.334 mmol), N-alpha-(N-t-butoxycarbonylphenylalanyl)-Nimidazole)-(t-butoxycarbonyl)histidine (168 mg., 0.334 mmol), 1-hydroxybenzotriazole (45 mg., 0.334 mmol) and dicyclohexylcarbodiimide (69 mg., 0.334 mol) were combined in 5 ml. $CH_2Cl_2$ at 0°, protected by a $CaCl_2$ drying tube, and stirred 18 hours at that temperature, then stripped of solvent, the residue triturated with 5 ml. ether and filtered. The ether filtrate was stripped to a residue (230 mg.) which was chromatographed on silica gel with 1% $CH_3OH$ in $CHCl_3$ as eluant to yield purified title product, 110 mg.; $^1$H-nmr ($CDCl_3$) includes delta 1.4 ppm (s, 9H, $C(CH_3)_3$).

EXAMPLE 29

2R,4S,5S-6-Cyclohexyl-5-[N-alpha-(N-t-butoxycarbonylphenylalanyl)histidyl]amino-2-(2-methylpropyl)-gamma-hexanolactone By the method of Example 26, title product of the preceding Example was converted to N-[2R,4S,5S-6-Cyclohexyl-5-(N-alpha-(N-t-butoxycarbonylphenylalanyl)-N (imidazole)-(t-butoxycarbonyl)histidyl)amino-4-hydroxy-2-(2-methylpropyl)hexanoyl]-proline methyl ester, 110 mg.; $^1$H-nmr showed loss of the histidine t-butoxycarbonyl protecting group. This intermediate product, when chromatographed on silica gel with 1:24 $CH_3OH:CHCl_3$ formed title product with loss of proline methyl ester, 51 mg.; $^1$H-nmr ($CDCl_3$) includes delta 1.4 ppm (s, 9H, $C(CH_3)_3$), but no methyl ester peak; ir ($CDCl_3$) includes lactone carbonyl at 1785 $cm^{-1}$.

EXAMPLE 30

2R,4S,5S-6-Cyclohexyl-5-[N-alpha-(N-t-butoxycarbonylphenylalanyl)histidyl]amino-4-hydroxy-2-(2-methylpropyl)hexanamide Title product of the preceding Example (32.7 mg.) on 0.5 ml. methanol was perfused with excess dry $NH_3$ at 0°. After about 10 minutes, the reaction mixture was stripped, the residue triturated with ether, and title product recovered as a white solid by filtration, 23 mg.; $^1$H-nmr ($CDCl_3$) includes delta 1.4 ppm (s, 9H, $C(CH_3)_3$).

EXAMPLE 31

N-[N-alpha-(t-butoxycarbonyl)-N-epsilon-(benzyloxycarbonyl)lysyl]statine Ethyl Ester By the method of Example 19, chromatographic purification being unnecessary, statine ethyl ester hydrochloride (0.467 g., 0.00195 mol), N-alpha-(t-butoxycarbnyl)-N-epsilon-(benzyloxycarbonyl) lysine 0.198 g., 0.00195 mol), N-methylmorpholine (0.215 ml., mg., 0.00195 mol), 1-hydroxybenzotriazole (264 mg., 0.00195 mol) and dicyclohexylcarbodiimide (403 mg., 0.00195 mol) in 25 ml. $CH_2Cl_2$ were converted to title product as a solid foam, 0.704 g.; tlc Rf 0.65 (9:1 $CHCl_3$: $CH_3OH$); $^1$H-nmr ($CDCl_3$) includes delta 1.4 ppm (s, 9H, $C(CH_3)_3$).

EXAMPLE 32

N-[N-epsilon-(Benzyloxycarbonyl)lysyl]statine Ethyl Ester Hydrochloride

The product of the preceding Example (0.805 g., 0.00142 mol) was stirred in 10 ml. 3.7N HCl in dioxane for 2 hours, stripped, the residue triturated with ether, and filtered to yield title product, 0.650 g.; $^1$H-nmr ($CD_3OD$) includes delta 5.2 ppm (s, 2H, benzyl-$CH_2$).

EXAMPLE 33

N-[N-alpha-(2R,4S,5S-6-Cyclohexyl-5-(t-butoxycarbonylamino)-4-(2-tetrahydropyranyloxy)-2-(2-methylpropyl)hexanoyl)-N-epsilon-(benzyloxycarbonyl)-lysyl]statine Ethyl Ester By the procedure of Example 28, using 0.5% methanol in $CHCl_3$ as eluant, the product of the preceding Example (332 mg., 0.662 mmol) and the product of Example 8 (311 mg., 0.662 mmol) were converted to chromatographed title product, 300 mg.; $^1$H-nmr ($CDCl_3$) includes delta 1.4 (s, 9H, $C(CH_3)_3$).

EXAMPLE 34

N-[N-alpha-(2R,4S,5S-6-Cyclohexyl-5-(t-butoxycarbonylamino)-4-hydroxy-2-(2-methylpropyl)hexanoyl)-N-epsilon-(benzyloxycarbonyl)lysyl]-statine Ethyl Ester By the procedure of Example 26, the product of the preceding Example (300 mg.) was converted to title product, chased with 2×10 ml. of toluene and dried under high vacuum, 200 mg.; $^1$H-nmr ($CDCl_3$) includes delta 1.4 ppm (s, 9H, $C(CH_3)_3$).

EXAMPLE 35

N-[N-alpha-(2R,4S,5S-6-Cyclohexyl-5-amino-4-hydroxy-2-(2-methylpropyl)hexanoyl)-N-epsilon(benzyloxycarbonyl)lysyl]statine Ethyl Ester The product of the preceding Example (200 mg.) and 10 ml. of 3.7N HCl in dioxane were stirred for 2 hours, stripped, the residue triturated with ether and white solids recovered by filtration. Chromatography of these solids on 35 g. silica gel using 1:19 $CH_3OH:CHCl_3$ gave HCl free title product, 52 mg.; $^1$H-nmr ($CD_3OD$) includes delta 5.2 (s, 2H, benzyl-$CH_2$).

EXAMPLE 36

N-[[N-alpha-[2R,4S,5S-6-Cyclohexyl-5-((N-alpha-(N-t-butoxycarbonylphenylalanyl)-N(imidazole)-(t-butoxycarbonyl)histidyl))amino-4-hydroxy-2-(2-methylpropyl)hexanoyl]-N-epsilon-[benzyloxycarbonyl]-lysyl]]statine Ethyl Ester Except to use 2 equivalents of 1-hydroxybenzotriazole and to use 2.5% $CH_3OH$ in $CHCl_3$ as eluant, the product of the preceding Example (52 mg., 0.0709 mmol) and N-alpha-(N-t-butoxycarbonylphenylalanyl)-N(imidazole)-(t-butoxycarbonyl)histidine (36 mg., 0.0709 mol) were converted to chromatographed, title product, 28 mg.; $^1$H-nmr ($CDCl_3$) includes delta 1.4 ppm (s, 9H, $C(CH_3)_3$); hplc retention time 10.28 minutes reverse phase C18 column eluting with 1:1 acetonitrile:pH 2.1 phosphate buffer at 3 ml/minute).

EXAMPLE 37

N-[[N-alpha-2R,4S,5S-6-Cyclohexyl-5-(N-butoxycarbonylphenylalanyl-histidyl)amino-4-hydroxy-2-(2-methylpropyl)hexanoyl]-N-epsilon-[benzyloxycarbonyl]lysyl]]statine Ethyl Ester By the method of Example 26, the product of the preceding Example (28 mg.) was converted to present title product, 22 mg.; $^1$H-nmr ($CDCl_3$) demonstrated loss of the imidazole t-butoxycarbonyl protecting group, but includes delta 1.4 ppm (s, 9H) due to the retained t-butoxycarbonyl group.

EXAMPLE 38

N-[[N-alpha-2R,4S,5S-6-Cyclohexyl-5-(N-t-butoxy-carbonylphenylalanyl-histidyl)amino-4-hydroxy-2-(2-methylpropyl)hexanoyl]lysyl]]statine Ethyl Ester The product of the preceding Example (22 mg.) was hydrogenated at atmospheric pressure in 2 ml. ethanol over 22 mg. 10% Pd/C for 3 hours. Catalyst was recovered by filtration over diatomaceous earth with 2×1 1 ml. ethanol wash. The combined filtrate and wash was stripped to a glass, converted to a white, filterable powder by trituration with minimal ether, 13 mg.; $^1$H-nmr (CDCl$_3$) includes delta 1.5 ppm (s, 9H, C(CH$_3$)$_3$).

EXAMPLE 39

2R,4S,5S-6-Cyclohexyl-5-(t-butoxycarbonylamino)-2-benzyl-gamma-hexanolactone

Under N$_2$, dry di(isopropyl)amine (2.48 ml., 0.0177 mol; distilled from CaH$_2$) in dry THF (7.4 ml., distilled from K) was cooled to 0°. Butyllithium (11.0 ml. of 1.62M in hexane, 0.0177 mol) was added dropwise over 5 minutes. After stirring 15 minutes at 0°, the mixture was cooled to −78° and the less polar 4S,5S-title product of Example 3 (2.30 g., 0.0074 mol) in 3.7 ml. dry THF added over 5 minutes. After stirring 30 minutes more at −78°, benzyl bromide (0.923 ml., 0.0078 mol) in 3.7 ml. dry THF was added dropwise over 5 minutes. After 1 hour at −78°, the reaction was quenched by the addition of 10 ml. saturated NH$_4$Cl, warmed to room temperature, diluted with 25 ml. ether and the layers separated. The organic layer was washed 2×15 ml. saturated NaHCO$_3$, dried (MgSO$_4$) and stripped to an oil (3.29 g.). The oil was chromatographed on 150 g. silica gel eluting with 2.5 liters 1:9 ethyl acetate:hexane and monitoring by tlc. Clean product fractions were combined and stripped to yield purified title product as a white oily solid, 1.46 g.; tlc Rf 0.60 (1:1 ethyl acetate:-hexane). More polar starting material (0.91 g. of yellow oil about 70% pure, tlc Rf 0.4 in the same system) was also recovered from the column.

EXAMPLE 40

2R,4S,5S-6-Cyclohexyl-5-(t-butoxycarbonylamino)-4-hydroxy-2-benzyl-N-methylhexanamide Title product of the preceding Example (157 mg.) was dissolved in 2 ml. CH$_3$OH, cooled to 0°, and perfused with CH$_3$NH$_2$ for 3 minutes. The flask was stoppered, allowed to stand at room temperature for 1.5 hours, stripped with 2×2 ml. ether chase and dried under high vacuum to yield title product as a white, solid foam, 164 mg.; tlc Rf 0.17 (1:1 ethyl acetate:hexane), Rf 0.29 (3:1 ethyl acetate:hexane); $^1$H-nmr (CDCl$_3$, 300MHz showed the expected C(CH$_3$)$_3$ (s, 9H), N-CH$_3$ (d, 3H), aromatic resonances and t-butoxycarbonyl-NH (d, 1H), peaks.

EXAMPLE 41

2R-,4S,5S-6-Cyclohexyl-5-amino-4-hydroxy-2-benzyl-N-methylhexanamide Hydrochloride The product of the preceding Example (159 mg.) was dissolved in 2 ml. 4N HCl in dioxane, stirred under N$_2$ 0.5 hour, stripped, chased 3×2 ml. ether and the residue dried under high vacuum to yield title product as a pale yellow powder, 135 mg.; tlc 0.20 (18:2:1 CHCl$_3$:ethanol:acetic acid; spotted plate exposed to NH$_3$ to neutralize HCl salt prior to elution).

EXAMPLE 42

2R,4S,5S-6-Cyclohexyl-5-[N-alpha-(N-t-butoxycarbonylphenylalanyl)-N(imidazole)-(t-butoxycarbonyl)-histidyl]amino-4-hydroxy-2-benzyl-N-methylhexanamide Title product of the preceding Example (123 mg., 0.333 mmol), CH$_2$Cl$_2$ (1 ml.), triethylamine 0.060 ml., 0.433 mmol), N-alpha-(N-t-butoxycarbonylphenylalanyl)-N (imidazole)-(t-butoxycarbonyl)histidine (176 mg., 0.350 mmol), 1-hydroxybenzotriazole (84 mg., 0.550 mmol) and dicyclohexylcarbodiimide (72 mg., 0.350 mmol) were sequentially combined at 0° and stirred under N$_2$ for 16 hours at that temperature. By-product DCU was recovered by filtration with 3 ml. CH$_2$Cl$_2$ wash. The combined filtrate and wash was washed 2×3 ml. 1N NaOH, and then 1×3 ml. brine, dried (MgSO$_4$), stripped to 342 mg. pale white solids, and chromatographed on 20 g. silica gel, gradiently eluting with 250 ml. each 0.5%, 1%, 2%, 4% and 6% ethanol in CH$_2$Cl$_2$ and monitoring by tlc to yield purified title product, 154 mg.; tlc Rf 0.55 (18:2:1 CHCl$_3$:ethanol:acetic acid).

EXAMPLE 43

2R,4S,5S-6-Cyclohexyl-5-(t-butoxycarbonylphenylalanyl-histidyl)amino-4-hydroxy-2-benzyl-N-methylhexanamide Title product of the preceding Example (147 mg.) was stirred under N$_2$ with 1.5 ml. of 4:1 acetic acid:H$_2$O for 7 hours, then stripped with 3×3 ml. ether chase and dried under high vacuum to yield title product as a white powder, 135 mg.; tlc Rf 0.05 (18:2:1 CH$_3$Cl$_3$:ethanol:acetic acid); $^1$H-nmr (DMSO-d$_6$), 250MHz includes delta (ppm): 1.32 (s, 9H, t-butyl); 3.72, 4.15 and 4.48 (3m, 1H, each); 6.87 and 7.52 (s, 1H, each, imidazolyl CH); 7.0–7.35 (m, aromatic), 7.40, 7.62 and 8.17 (3d, 1H each).

EXAMPLE 44

2R,4S,5S-6-Cyclohexyl-5-(t-butoxycarbonylamino-4-hydroxy-2-(cyclohexylmethyl)-N-methylhexanamide Title product of Example 40 (83.1 mg.) was hydrogenated over 45 mg. of 10% Rh/C in 10 ml. methanol under 4 atmospheres of H$_2$ for 1.5 hours. Catalyst was recovered by filtration over diatomaceous earth with methanol wash. The combined filtrate and wash was stripped, chased 2×5 ml. ether and dried in high vacuum to yield title product as a white, solid foam, 76.9 mg.; $^1$H-nmr (CDCl$_3$, 300MHz) includes C(CH$_3$)$_3$ singlet, no phenyl protons, and N-CH$_3$ doublet; tlc Rf 0.32 (3:1 ethyl acetate:hexane).

EXAMPLE 45

2R,4S,5S-6-Cyclohexyl-5-amino-4-hydroxy-2-(cyclohexylmethyl)-N-methylhexanamide Hydrochloride By the method of Example 41, title product of the preceding Example (75 mg.) was converted to present title product, 64.1 mg.; tlc Rf 0.18 (18:2:1 CHCl$_3$:ethanol:acetic acid; spotted plate neutralized with NH$_3$ vapor before elution).

EXAMPLE 46

2R,4S,5S-6-Cyclohexyl-5-[N-alpha-(N-t-butoxycarbonylphenylalanyl)-N(imidazole)-(t-butoxycarbonyl)-histidyl]amino-4-hydroxy-2-(cyclohexylmethyl)-N-methylhexanamide By the method of Example 42, the product of the preceding Example (59.1 mg., 0.158 mmol) was converted to chromatographed title product as a white, solid foam, 76.4 mg.; tlc Rf 0.60 (18:2:1 CHCl$_3$:ethanol:acetic acid); $^1$H-nmr (DMSO-d$_6$, 250 MHz) includes two C(CH$_3$)$_3$ singlets centered at 1.6 ppm.

EXAMPLE 47

2R,4S,5S-6-Cyclohexyl-5-(t-butoxycarbonylphenylalanyl-histidyl)amino-4-hydroxy-2-(cyclohexylmethyl)-N-methylhexanamide By the method of Example 43, the product of the preceding Example (71.5 mg.) was converted to title product as a white powder, 59.1 mg.; tlc Rf 0.05 (18:2:1 CHCl$_3$, ethanol:acetic acid), $^1$H-nmr DMSO-d$_6$, 250MHz) includes C(CH$_3$)$_3$ singlet at 1.32 ppm, N-CH$_3$ doublet at 2.58 ppm and imidazole C-H singlets at 6.86 and 7.52 ppm.

EXAMPLE 48

2R,4S,5S-6-Cyclohexyl-5-(t-butoxycarbonylamino)-4-hydroxy-2-(2-methylpropyl)-N-benzylhexanamide Title product of Example 5 (150 mg., 0.408 mmol), dry toluene (2 ml.), benzylamine (0.29 ml., 5 equivalents), acetic acid (0.023 ml., 1 equivalent) were stirred under N$_2$, gradually heated to 90° and held at that temperature for 6 hours. The reaction mixture was cooled, diluted with 3 ml. ethyl acetate, washed 2×3 ml. 1N HCl and 1×3 ml. brine, dried (MgSO$_4$) and stripped to yield title product as a white, oily foam, 187 mg.; tlc Rf 0.58 (2:1 ethyl acetate:hexane).

EXAMPLE 49

2R,4S,5S-6-Cyclohexyl-5-amino-4-hydroxy-2-(2-methylpropyl)-N-benzylhexanamide Hydrochloride By the method of Example 41, the product of the preceding Example (172 mg.) was converted to present title product as a white powder, 146 mg.; tlc Rf 0.30 (18:2:1 CHCl$_3$:ethanol:acetic acid; spotted plate exposed to NH$_3$ vapor prior to elution).

EXAMPLE 50

2R,4S,5S-6-Cyclohexyl-5-[N-alpha-(N-t-butoxycarbonylphenylalanyl)-N(imidazole)-(t-butoxycarbonyl)-histidyl]amino-4-hydroxy-2-(2-methylpropyl)-N-benzylhexanamide By the method of Example 42, the product of the preceding Example (136 mg., 0.331 mmol) was converted to chromatographed title product as a white, solid foam, 167 mg.; tlc Rf 0.60 (18:2:1 CHCl$_3$:ethanol:acetic acid).

EXAMPLE 51

2R,4S,5S-6-Cyclohexyl-5-(t-butoxycarbonylphenylalanyl-histidyl)amino-4-hydroxy-2-(2-methylpropyl)-N-benzylhexanamide By the method of Example 43, the product of the preceding Example was converted to present title product as a white, solid foam, 146 mg.; tlc Rf 0.18 (18:2:1 CHCl$_3$:ethanol:acetic acid); $^1$H-nmr (DMSO-d$_6$), 250MHz) includes delta (ppm): 0.83 and 0.90 (d, 3H, each, J=6Hz, C(CH$_3$)$_2$); 1.32 (s, 9H, C(CH$_3$)$_3$); 3.72, 4.16 and 4.50 (m 1H, each); 4.28 (m, 2H, NCH$_2$); 6.86 (br, 1H), 7.52 (s, 1H); 7.1-7.4 (m, 11-13H, aromatic and NH); 8.25 (d, 1H, NH); 8.36 (t, 1H).

EXAMPLE 52

2R,4S,5S-6-Cyclohexyl-5-(t-butoxycarbonylamino)-4-hydroxy-2-(2-methylpropyl)-N,N-dimethylhexanamide Title product of Example 5 (595 mg.) was dissolved in 5 ml. methanol, chilled to 10°, perfused with dimethylamine for 3 minutes, stoppered and allowed to stand at room temperature for 1.5 hours Tlc indicated 80% conversion. At room temperature the solution was then perfused for 2 minutes with dimethylamine, restoppered, and allowed to stand 18 hours, at which time tlc indicated complete conversion. The solution was stripped and the residue dried under high vacuum to yield title product as a white, solid foam, 112 mg.; tlc Rf 0.31 (3:1 ethyl acetate:hexane); ms includes peaks at 281.0, 230.9, 212.0, 186.1, 131.0, 100.0, 80.9, 68.9 and 57.0.

EXAMPLE 53

2R,4S,5S-6-Cyclohexyl-5-amino-4-hydroxy-2-(2-methylpropyl)-N,N-dimethylhexanamide Hydrochloride By the method of Example 41, the product of the preceding Example (107 mg.) was converted to present title product as an off-white, solid foam, 94.7 mg.; tlc Rf 0.16 (18:2:1 CHCl3:ethanol:acetic acid; spotted plate exposed to NH$_3$ vapor prior to elution); ms includes 313.3, 256 1, 215.2, 186.1, 156.0, 143.1, 26.1, 111.1, 100.1, 83.0 and 69.1.

EXAMPLE 54

2R,4S,5S-6-Cyclohexyl-5-[N-alpha-(N-t-butoxycarbonylphenylalanyl)-N(imidazole)-(t-butoxycarbonyl)-histidyl]amino-4-hydroxy-2-(2-methylpropyl)-N,N-dimethylhexanamide By the method of Example 42, additionally using 250 ml. each of 8%, 12%, 20% and 50% ethanol in CH$_2$Cl$_2$ for chromatographic elution, the product of the preceding Example (87 mg., 0.249 mmol) was converted to present title product as a white, solid foam, 107 mg.; tlc Rf 0.52 (18:2:1 CHCl$_3$:ethanol:acetic acid); $^1$H-nmr (DMSO-d$_6$, 250 MHz) include two C(CH$_3$)$_3$ singlets, aromatic peaks and imidazole peaks; ms 511.4, 357.3, 329.1, 301.2, 257.0, 211.1, 165.1, 136.0, 120.1, 110.0, 91.0, 57.1, 41.0.

EXAMPLE 55

2R,4S,5S-6-Cyclohexyl-5-(t-butoxycarbonylphenylalanyl-histidyl)amino-4-hydroxy-2-(2-methylpropyl)-N,N-dimethylhexanamide By the method of Example 43, the product of the product of the preceding Example was converted to crude title product, 78.2 mg., containing a substantial mp impurity by hplc. The crude product was subjected to preparative hplc on a 5 g. reverse phase C-18 column, eluted with four column volumes each of 1:1, 3:1, 17:3 and 100:0 methanol:H$_2$O. The impurity eluted with the 3:1 eluant, while purified title product eluted with the 17:3 eluant, isolated by stripping as a white powder, 46.0 mg.; tlc Rf 0.02 (18:2:1 CHCl$_3$:ethanol:acetic acid); hplc retention time 5.87 minutes (C-8 4.6 mm×25 cm.

column, eluted with 3:2 CH₃CN:pH 2.1 phosphate buffer at 1.5 ml/min.); ms 322.4, 311.1, 283.1, 218.9, 165.1, 131.0, 110.1, 97.0, 91.0, 69.1, 59.1, 43.0; $^1$H-nmr (DMSO-d$_6$, 250 MHz) includes delta 1.32 (s, 9H, C(CH$_3$)$_3$, 2.85 and 3.07 (2s, 6H, N(CH$_3$)$_2$), 6.92 and 7.52 (2s, 2H, imidazole C-H).

EXAMPLE 56

5-[2R,4S,5S-6-Cyclohexyl-5-(t-butoxycarbonylamino)-4-(2-tetrahydropyranyloxy)-2-(2-methylpropyl)hexanoyl]amino-1-(benzyloxycarbonylamino)pentane By the method of Example 31, except to use ether in place of ethyl acetate in isolation, title product of Example 8 (160 mg., 0.341 mmol) and of Preparation 3 (80.5 mg., 0.341 mmol) were converted to present title product, 222 mg.; $^1$H-nmr (CDCl$_3$) includes delta 1.4 ppm (s, 9H, C(CH$_3$)$_3$).

EXAMPLE 57

5-[2R,4S,5S-6-Cyclohexyl-5-(t-butoxyamino)-4-hydroxy-2-(2-methylpropyl)hexanoyl]amino-1-(benzylcarbonylamino)pentane By the method of Example 26, the product of the preceding Example (221 mg.) was converted to present title product, 193 mg.; $^1$H-nmr (CDCl$_3$) includes delta 1.4 ppm (s, 9H, C(CH$_3$)$_3$).

EXAMPLE 58

5-[2R,4S,5S-6-Cyclohexyl-5-amino-4-hydroxy-2-(2-methylpropyl)hexanoyl]amino-1-(benzyloxycarbonylamino)pentane The product of the preceding Example (193 mg.) was stirred with 10 ml. 3.7N HCl in dioxane for 2 hours, stripped and the residue triturated with ether to yield title product, 144 mg.; $^1$H-nmr (CD$_3$OD) includes delta 5.2 ppm (s, 2H, benzyl CH$_2$).

EXAMPLE 59

5-[[2R,4S,5S-6-Cyclohexyl-5-[N-alpha-(N-t-butoxycarbonylphenylalanyl)-N(imidazole)-t-butoxycarbonyl)-histidyl]amino-4-hydroxy-2-(2-methylpropyl)hexanoyl]]amino-1-(benzylcarbonylamino)pentane Using CHCl$_3$ as eluant, the method of Example 28 was employed to convert the product of the preceding Example to present chromatographed title product, 25 mg.; $^1$H-nmr (CDCl$_3$) includes delta 1.4 ppm s, 9H, C(CH$_3$)$_3$.

EXAMPLE 60

5-[2R,4S,5S-6-Cyclohexyl-5-(t-butoxycarbonylphenylalanyl-histidyl)amino-4-hydroxy-2-(2-methylpropyl)hexanoyl]amino-1-(benzyloxycarbonylamino)-pentane By the method of Example 43, title product of the preceding Example (25 mg.) was converted to present title product, the residue after stripping was chased twice with toluene and the residue triturated with ether to yield title product as white solids, 11 mg.; $^1$H-nmr (CDCl$_3$) includes delta 1.4 ppm (s 9H, C(CH$_3$)$_3$).

Hydrogenation over Pd/C according to Example 13 is used to convert this product to 5-[2R,4S,5S-6-Cyclohexyl-5-(t-butoxycarbonylphenylalanyl-histidyl)amino-4-hydroxy-2-(2-methylpropyl)hexanoyl]aminopentylamine.

EXAMPLE 61

Benzyl4-[2R,4S,5S-6-Cyclohexyl-5-(t-butoxycarbonylamino)-4-(2-tetrahydropyranyloxy)-2-(2-methylpropyl)hexanoyl]aminobutyrate Title product of Example 8 (160 mg., 0.341 mmol) and benzyl 4-aminobutyrate hydrochloride (66 mg., 0.341 mmol) were coupled according to the procedure of Example 23. At the end of the reaction period, the mixture was stripped and the residue taken up in 5 ml. ether, washed 1×3 ml. saturated NaHCO$_3$, 1×3 ml. 5% HCl and 1×3 ml. brine, and restripped to crude product, 172 mg., which was chromatographed on 20 g. silica gel with CHCl$_3$ as eluant to yield purified title product, 107 mg.; $^1$H-nmr (CDCl$_3$) includes delta 1.4 ppm (s, 9H, C(CH$_3$)$_3$).

EXAMPLE 62

Benzyl 4-[2R,4S,5S-6-Cyclohexyl-5-(t-butoxycarbonylamino)-4-hydroxy-2-(2-methylpropyl)hexanoyl]aminobutyrate By the method of Example 43, the product of the preceding Example (380 mg.) was converted to present title product, 330 mg.; $^1$H-nmr includes delta 1.4 ppm (s, 9H, C(CH$_3$)$_3$).

EXAMPLE 63

Benzyl 4-[2R,4S,5S-6-Cyclohexyl-5-amino-4-hydroxy-2-(2-methylpropyl)hexanoyl]aminobutyrate The product of the preceding Example (330 mg.) in 10 ml. of 3.7N HCl in dioxane was allowed to stand for 2 hours. The mixture was stripped, the residue was taken up in 5 ml. ethyl acetate, washed with 5 ml. each of saturated NaHCO$_3$ and then brine, dried (MgSO$_4$) and restripped to yield title product as an oil, 220 mg.; $^1$H-nmr (CD$_3$OD) includes delta 5.2 ppm (s, 2H, CH$_2$C$_6$H$_5$).

EXAMPLE 64

Benzyl 4-[[2R,4S,5S-6-Cyclohexyl-5-[N-alpha-(N-(t-butoxycarbonyl)phenylalanyl)-N(imidazole)(t-butoxycarbonyl)-histidyl]amino-4-hydroxy-2-(2-methylpropyl)hexanoylamino]butyrate By the method of Example 42, the product of the preceding Example (270 mg., 0.586 mmol) was coupled to form title product. Following recovery of DCU, the filtrate was stripped, taken up in ether, refiltered, and the filtrate stripped to 480 mg. of crude product. The latter was chromatographed on 50 g. silica gel using 2.5% methanol in CHCl$_3$ as eluant to yield purified title product, 132 mg.; $^1$H-nmr (CDCl$_3$) includes delta 1.4 ppm (s, 9H, C(CH$_3$)$_3$).

EXAMPLE 65

4-[2 5S-6-Cyclohexyl-5-(N-(t-butoxycarbonyl)phenylalanyl-histidyl)amino-4-hydroxy-2-(2-methylpropyl)hexanoylamino]butyric Acid The product of the preceding Example (93 mg.) was hydrogenated in 2.5 ml. of 1:1 ethyl acetate:methanol over 23 mg. of 10% Pd/C for 2 hours at 4 atmospheres. Catalyst was recovered by filtration and the filtrate stripped to an oil, which was taken up in ether, filtered and restripped to yield title product, 62 mg.; $^1$H-nmr (CD$_3$OD) includes delta 1.4 ppm (s, 9H, C(CH$_3$)$_3$).

EXAMPLE 66

2R,4S,5S-6-Cyclohexyl-5-(t-butyloxycarbonylamino)-2-[(2-naphthyl)methyl]-gamma-hexanolactone By the method of Example 39, title product of Example 3 (0.295 g., 0.95 mmol) and 2-(bromomethyl)naphthalene (220 mg., 0.99 mmol) were converted to crude title product (0.43 g. of yellow oil) which was chromatographed on 20 g. silica gel, eluting with 700 ml. 1:9 ethyl acetate:hexane and then 300 ml. 1:1 ethyl acetate:hexane, monitoring by tlc. Clean title product was isolated from center cuts, 139 mg.; Rf 0.62 (1:1 ethyl acetate:hexane).

EXAMPLE 67

2R,4S,5S-6-Cyclohexyl-5-(t-butoxycarbonylamino)-4-hydroxy-2-[(2-naphthyl)methyl]-N-methylhexanamide Title product of the preceding Example (113 mg.) in 2 ml. of methanol was chilled to 0°-5° and the cold solution perfused with CH$_3$NH$_2$ for 2 minutes, stoppered, allowed to stand at ambient temperature for 2 hours, stripped, chased 2×2 ml. ether and dried under high vacuum to yield title product as a white foam, 114 mg.; tlc Rf 0.15 (1:1 ethyl acetate:hexane), Rf 0.48 (18:2:1 CHCl$_3$:ethanol:acetic acid).

EXAMPLE 68

2R,4S,5S-6-Cyclohexyl-5-amino-4-hydroxy-2-[(2-naphthyl)methyl]-N-methylhexanamide Hydrochloride By the method of Example 15, costripping with ether, the product of the preceding Example 107.4 mg., was converted to present title product, a solvent wet yellow powder, 102.5 mg., Rf 0.2 (18:2:1 CHCl$_3$:ethanol:acetic acid; loaded plate preneutralized with NH$_3$ vapor).

EXAMPLE 69

2R,4S,5S-6-Cyclohexyl-5-(N-(N-alpha-(N-t-butoxycarbonyl)phenylalanyl)-N(imidazole)-(t-butoxycarbonyl)-histidyl]amino-4-hydroxy-2-[(2-naphthyl)methyl]-N-methylhexanamide By the method of Example 16, title product of the preceding Example (96 mg. 0.229 mmol) and title product of Preparation 1 (121 mg., 0.240 mmol) were converted to crude title product as an oily foam, 235 mg., which was chromatographed on 5 g. silica gel, eluting with 200 ml. each of 0.5%, 1%, 2%, 4% and 6% ethanol in CH$_2$Cl$_2$ and monitoring by tlc. Clean product fractions were stripped to yield purified title product a a white foam, 124 mg., tlc Rf 0.6 (18:2:1 CHCl$_3$:ethanol:acetic acid).

EXAMPLE 70

2R,4S,5S-Cyclohexyl-5-(N-t-butoxycarbonylphenylalanyl-histidyl)amino-4-hydroxy-2-[(2-naphthyl)methyl)-N-methylhexanamide Title product of the preceding Example (116 mg.) in 1.5 ml. methanol was stirred with a K$_2$CO$_3$ (1 mg.) for 1 hour, then neutralized with 2 drops of acetic acid. The mixture was costripped with ether to yield title product as a white powder, 101.4 mg.; tlc Rf 0.08 (18:2:1:ethanol:acetic acid); ms no m+ but includes mass peaks 311.1, 283.0, 257.0, 213.0, 192.1, 179.1, 141.0, 111.0, 97.1 and 57.1; $^1$H-nmr (DMSO-d$_6$) delta (300 MHz), 1.30 (s, 9H, C(CH$_3$)$_3$), 2.46 (d, 3H, NCH$_3$), 3.70, 4.14, 4.47 (3m, 1H each), 6.86, 7.62 (2s, 1H each), 7.10, 8.22 (2d, 1H each), 7.15–7.41 (m, aromatic), 7.48, 7.84 (2m, aromatic).

EXAMPLE 71

2R,4S,5S-6-Cyclohexyl-5-[[N-[N-alpha-methyl-N-alpha-(N-t-butoxycarbonylphenylalanyl)-N(imidazole)(t-butoxycarbonyl)]histityl]]amino-4-hydroxy-2-(2-(2-methylpropyl)-N,N-dimethylhexanamide By the methods of Examples 16 end 69, the product of Example 53 (0.534 g., 0.00153 mol) and N-alpha-methyl-N-alpha-(N-t-butoxycarbonylphenylalanyl)-N(imidazole)-(t-butoxycarbonyl)histidine (0.790 g., 0.00153 mol) were converted to present, chromatographed product as an off-white foam, 0.394 g. tlc Rf 0.52 (18:2:1:ethanol:acetic acid).

EXAMPLE 72

2R,4S,5S-6-Cyclohexyl-5-[N-alpha-methyl-N-alpha-(N-(t-butoxycarbonyl)phenylalanyl)histidyl]amino-4-hydroxy-2-(2-(2-methylpropyl)-N,N-dimethylhexanamide By the method of Example 70, the product of the preceding Example (195 mg.) was converted to present title product, purified by preparative hplc on an RP C-18 column, eluting with 4 column volumes of 1:1 CH$_3$OH:H$_2$O and 6 column volumes of 3:1 CH$_3$OH:H$_2$O. Clean product fractions were found in the latter eluant, recovered as a white powder by stripping, 153.6 mg.; tlc Rf 0.09 (18:2:1 CHCl$_3$:ethanol:acetic acid); ms no m+ but includes 575.3, 525.3, 511.3, 472.3, 442.2, 416.2, 399.2, 288.2, 371.2, 343.1, 291.0, 247.1, 186.1, 165.1, 123.9, 109.0, 95.0, 69.1, 59.0, 43.0; $^1$H-nmr (DMSO-d$_6$) delta (300 MHz) 0.78 (2d, 6H (CH$_3$)$_2$ rotamers), 3.0 (3s, 3H), 3.10, 3.76, 4.50, 4.60, 4.95, 5.10, 6.92, 7.48, 7.60 (multiplets), 7.10–7.35 (broad multiplets, aromatic).

EXAMPLE 73

N-alpha-[2R,4S-5S-6-Cyclohexyl-5-(t-butoxycarbonyl)amino-4-(2-tetrahydropyranyloxy)-2-(2-methylpropyl)hexanoyl]-N-epsilon-[benzyloxycarbonyl]]lysine Methyl Ester Title product of Example 8 (0.318 g., 0.00068 mol) was coupled with N-epsilon-(benzyloxycarbonyl)lysine methyl ester hydrochloride (0.223 g., 0.00068 mol) according to the method of Example 9. The crude product (0.261 g.) was purified by chromatography on 30 g silica gel with 99:1 CHCl$_3$:CH$_3$OH as eluant to yield purified title product, 0.147 g.; $^1$H-nmr (CDCl$_3$) includes delta 3.8 (s, 3H, OCH$_3$).

EXAMPLE 74

N-alpha-[2R,4S,5S-6-Cyclohexyl-5-(t-butoxycarbonyl)amino-4-hydroxy-2-(2-methylpropyl)hexanoyl]-N-epsilon[benzyloxycarbonyl]]lysine Methyl Ester Title product of the preceding Example (0.131 g., 0.00018 mol) was stirred in 5 ml. 4:1 acetic acid:H$_2$O for 16 hours, then stripped with toluene chase to yield title product as a white solid, 95 mg.; $^1$H-nmr (CDCl$_3$) includes delta 3.8 (s, 3H, OCH$_3$).

EXAMPLE 75

N-alpha-[2R,4S,5S-6-Cyclohexyl-5-amino-4-hydroxy-2-(2-methy[propyl)hexanoyl]-N-epsilon-[benzyloxycarbonyl]]lysine Methyl Ester Title product of the preceding Example (95 mg.) was dissolved in 2 ml. of trifluoroacetic acid at 0° C., held for 1 hour, stripped with toluene chase, the residue distributed between 10 ml. of ethyl acetate and 10 ml. saturated bicarbonate, the aqueous layer extracted 2×10 ml. fresh ethyl acetate, and the organic layers combined and washed with brine, dried over $MgSO_4$ and stripped to yield title product as an oil, 80 mg.; $^1$H-nmr ($CDCl_3$) includes delta 3.8 (s, 3H, $OCH_3$).

EXAMPLE 76

N-alpha-[[2R,4S,5S-6-Cyclohexyl-5-[N-alpha-(2-benzyl-3-phenylpropionyl)-N(imidazole)-(t-butoxycarbonyl)histidyl]amino-4-hydroxy-2-(2-methylpropyl)-hexanoyl]]-N-epsilon-[[benzyloxycarbonyl]]lysine Methyl Ester By the method of Examples 16 and 69, except to use 99:1 $CHCl_3$:$CH_3OH$ as eluant on chromatography, the product of the preceding Example, (80 mg., 0.142 mmol) and the product of Preparation 9 (70 mg., 0.142 mmol) were coupled to form the present title product, 113 mg. crude, 80 mg. chromatographed; $^1$H-nmr ($CDCl_3$) include delta 1.6 (s, 9H, $C(CH_3)_3$).

EXAMPLE 77

N-alpha-[[2R,4S,5S-6-Cyclohexyl-5-[N-alpha-(2-benzyl-3-phenylpropionyl)histidyl]amino-4-hydroxy-2-(2-methylpropyl)hexanoyl]]-N-epsilon-[[benzyloxycarbonyl]]lysine Methyl Ester The product of the preceding Example (80 mg.) was dissolved in 3 ml. of 4:1 acetic acid:$H_2O$, held for 24 hours, stripped with toluene chase, triturated with 3 ml. 1:1 ether:hexane and filtered to yield title product as a white powder, 40 mg.; $^1$H-nmr ($CDCl_3$) shows no $C(CH_3)_3$ peaks and includes delta 3.8 (s, 3H, $OCH_3$).

EXAMPLE 78

N-alpha-[[2R,4S,5S-6-Cyclohexyl-5-[N-alpha-(2-benzyl-3-phenylpropionyl)histidyl]amino-4-hydroxy-2-(2-methylpropyl)hexanoyl]]lysine Methyl Ester The product of the preceding Example (40 mg.) in 1 ml. methanol and 1 ml. acetic acid was hydrogenated over 40 mg. of 10% Pd/C for 1.5 hours. The catalyst was recovered by filtration and the filtrate stripped to an oil, chased twice with toluene to yield a white powder which was triturated with ether and filtered to yield present title product, 18 mg.; $^1$H-nmr ($CD_3OD$) includes delta 3.8 ppm (s, 3H).

By the method of Example 30, this product is converted to the corresponding lysine amide derivative.

EXAMPLE 79

S-4-Methyl-2-(t-butoxycarbonylamino)pentanal

By the method of Example 1, N-(t-butoxycarbonyl)-leucine methyl ester (28.0 g., 0.114 mol) was converted to present title product, 21.7 g. (88%), as a pale yellow oil; tlc Rf 0.36 (2:3 ethyl acetate:hexane); $^1$H-nmr ($CDCl_3$) delta (90 MHz) 0.97 (d, J=6, 6H), 1.1–1.8 (m, 3H), 1.4 (s, 9H), 3.3–5.0 (m, 2H), 9.53 (s, 1H).

EXAMPLE 80

Ethyl 4RS,5S-7-Methyl-5-(t-butoxycarbonylamino)-4-hydroxy-2-octynoate

By the method of Example 2, except to use gradient elution with 3:17 to 1:4 ethyl acetate:hexane on chromatography, the product of the preceding Example (0.4 g., 0.048 mol) was converted to present title product, 5.45 g., tlc Rf 0.40 (3:7 ethyl acetate: hexane); ir ($CHCl_3$) 3438, 3340, 2233, 1711 $cm^{-1}$; $^1$H-nmr ($CDCl_3$) delta (300 MHz) 0.97 (t, J=7, 6H), 1.34 (t, J=6, 3H), 1.48 (s, 9H), 1.48 (m, 2H), 1.70 (m, 1H), 3.3–3.4 (m, 1H), 3.81–3.96 (m, 1H), 4.28 (q, J=7, 2H), 4.45–4.58 (m, 1H), 4.68–4.78 (m, 1H).

Anal. Calcd. for $C_{16}H_{27}NO_5$: C, 61.32; H, 8.68; N, 4.47 Found: C, 61.38; H, 8.58; N, 4.42

EXAMPLE 81

4S,5S-7-Methyl-5-(t-butoxycarbonylamino)gamma-octanolactone

By the methods of Example 3, except to use gradient eluting with 2:3 to 1:0 ethyl acetate:hexane on chromatography, the product of the preceding Example was converted to the desired less polar (4S,5S)lactone product, crystallized by trituration with hexane, 3.10 g. (78%); m.p. 76°–77°; ir ($CHCl_3$) 3439, 1775, 1711 $cm^{-1}$; $^1$H-nmr ($CDCl_3$) delta (300 MHz) 0.92 (d, J=6, 6H), 1.44 (s, 9H), 1.28–1.81 (m, 3H), 2.06–2.32 (m, 2H), 2.48–2.58 (m, 2H), 3.79–3.92 (broad s, 1H), 4.42–4.58 (m, 2H).

Anal. Calcd. for $C_{14}H_{25}NO_4$: C, 61.97; H, 9.29; N, 5.16 Found: C, 62.15; H, 9.26; N, 5.12.

The more polar (4R,5S)lactone was also isolated in the chromatography in much lower yield and crystallized by hexane trituration, 0.68 g., m.p. 113.5°–116° C.

EXAMPLE 82

2R,4S,5S-7-Methyl-5-(t-butoxycarbonylamino)-2-(2-methyl-2-propenyl)-gamma-octanolactone Method A By the method of Example 4, the title product of the preceding Example (the less polar 4S,5S-epimer; 0.51 g., 0.0019 mol) was converted to present title product, in major portion, together with its more polar, 2S,4S,5S-epimer. The crude products (0.60 g.) were separated by chromatography on a 4.5×20 cm. column of silica gel, eluting with 1 l. each of 1:9, 3:17, 1:5, 1:4, 3:7 and 1:1 ether:hexane, collecting 23 ml. fractions. Fractions 51–85 gave purified title product, 0.21 g.; m.p. 128°–132°;

$[alpha]_D^{30}$ −23.7° (c = 0.529, $CH_3OH$)

More polar 2S,4S,5S-epimer was isolated from fractions 89–120, 105 mg.; $^1$H-nmr ($CDCl_3$) includes delta 4.8 (2s, 2H, vinyl protons) and 1.75 (s, 3H, vinyl methyl); a portion of this epimer was crystallized by slow evaporation from $CH_2Cl_2$:hexane, providing needle crystals, m.p. 99°–101°.

Method B

To a suspension of lithium hexamethyldisilazide at −78° C., prepared by the dropwise addition of 5.1 ml. (8.11 mmol) a 1.6M solution of n-butyllithium in hexane to 1.79 ml. (1.39 g., 8.49 mmol) of hexamethyldisilazane in 3.5 ml. of THF at 0° C., was added dropwise a solution of 1.00 g. (3.69 mmol) of 4S,5S-lactone of the preceding Example in 3 ml. of THF. At the end of the addition the mixture became clear and it was allowed to stir an additional 15 minutes at $-78°$ C. A solution of 0.548 g. (4.06 mmol) of freshly distilled methallyl bromide in 2 ml. of THF was then added dropwise over 5 minutes, and the mixture was allowed to slowly warm to $-40°$ C. over 2 hours before being quenched with 2 ml. of saturated NH$_4$Cl. After warming to room temperature the reaction mixture was partitioned between 30 ml. of ether and 30 ml. of 10% citric acid. The organic layer was separated and washed with 10% citric acid (3×30 ml.) and saturated NaHCO$_3$, dried (MgSO$_4$), and evaporated to 1.11 g. of a crude mixture of cis(2S) and trans(2R). These lactones were separated on 88 g. of silica gel with an ether-hexane (1:9 to 3:7) eluant. The fractions containing the less polar trans (2S)lactone [tlc Rf 0.55 (1:1 ether:hexane)] were combined and evaporated to 0.613 g. (51%) of a white solid, m.p. 132°–135° C. Minor impurities (as indicated by tlc) were removed by trituration in hexane to afford 0.562 g. (47%) of analytically pure title 2R,4S,5S-lactone, m.p. 133°–135° C. Crystals suitable for X-ray analysis were prepared by slow evaporation from hexane-methylene chloride. $^1$H-nmr (CDCl$_3$) delta (250 MHz) 0.90 (J, J=6, 3H), 0.92 (d, J=6, 3H), 1.42 (s, 9H), 1.70 (s, 3H), 1.92–2.15 (m, 2H), 2.26–2.39 (m, 1H), 2.57 (dd, J=15 and 3, 1H), 2.72–2.88 (m, 1H), 3.77–3.90 (m, 1H), 4.34 (d, J=9, 1H), 4.33–4.51 (m, 1H), 4.70 (s, 1H), 4.81 (s, 1H); $^{13}$C-nmr (75 mHz) delta 21.8, 23.0, 24.7, 28.3, 30.0, 37.9, 39.5, 41.8, 51.7, 79.8, 80.7, 112.8, 141.9, 156.0, 179.3; IR (CHCl$_3$) 3439, 1768, 1712, 1654 cm$^{-1}$; [alpha]$_D$ $-25.0°$ (C=0.5, CH$_3$OH). Anal. Calcd. for C$_{18}$H$_{31}$NO$_4$: C, 66.43; H, 9.60; N, 4.30. Found: C, 66.47; H, 9.59; N, 4.27. Single crystal X-ray analysis proved that the structure and stereochemical assignment of this compounds was correct.

The fractions containing the more polar cis(2S) lactone (tlc Rf 0.44 1:11 ether:hexane) were combined and evaporated to 39 mg (3%) of a white solid, mp 96°–98° C.; $^1$H-nmr (CDCl$_3$) delta (250 MHz) 0.92 (d, J=6, 6H), 1.43 (s, 9H), 1.72 (s, 3H), 2.02–2.14 (m, 1H), 2.23–2.36 (m, 1H), 2.60–2.87 (m, 2H), 3.74–3.89 (m, 1H), 4.35–4.47 (m, 2H), 4.69 (s, 1H), 4.78 (s, 1H); $^{13}$nmr (75 MHz) delta 21.9, 22.0, 23.0, 24.8, 28.3, 30.7, 38.8, 38.9, 42.3, 50.1, 79.6, 80.4, 112.6, 142.0, 155.9, 178.7; IR (CHCl$_3$) 3443, 1774, 1714, 1656 cm$^{-1}$; [alpha]$_D$ $-0.6°$ (C=0.5, CH$_3$OH). Anal. Calcd. for C$_{18}$H$_{31}$NO$_4$: C, 66.43; H, 9.60; N, 4.30. Found: C, 66.94; H, 9.45; N, 4.27.

EXAMPLE 83

2R,4S,5S-7-Methyl-5-(t-butoxycarbonylamino)-2(2-methylpropyl)-gamma-octanolactone An ethyl acetate (10 ml) solution of 438 mg. (1.35 mmol) of the title lactone of the preceding Example containing 44 mg. of 10% Pd/C was hydrogenated on a Parr Shaker apparatus at 50 psi for 2 hours. After filtration of the catalyst and evaporation of the solvent, 437 mg. (99%) of present title product was obtained as a white solid, mp 130°–131° C. $^1$H-nmr (CDCl$_3$) delta (300 MHz) 0.84–0.97 (m, 12H), 1.41 (s, 9H), 1.86–1.96 (m, 1H), 2.30–2.42 (m, 1H), 2.56–2.68 (m, 1H), 3.76–3.89 (m, 1H), 4.35 (d, J=8, 1H), 4.45 (broad t, 1H); $^{13}$C-nmr (75 Hz) delta 21.3, 21.8, 22.9, 23.0, 24.8, 26.1, 28.3, 31.0, 37.7, 40.5, 41.9, 51.7, 79.8, 80.5, 156.0, 180.3; IR [CHCl$_3$] 3439, 1769, 1713 cm$^{-1}$; [alpha]$_D$ $-32.1°$ (C=1.0, CH$_3$OH). Anal. Calcd. for C$_{18}$H$_{33}$NO$_4$: C, 66.02; H, 10.16; N, 4.28. Found: C, 66.07; H, 10.03; N, 4.05.

By the various procedures of the preceding Examples, the present product is converted to analogous renin inhibiting products wherein R$^1$ is 2-methylpropyl rather than cyclohexylmethyl.

EXAMPLE 84

Benzyl 3-[2R,4S,5S-6-Cyclohexyl-5-(t-butoxycarbonylamino)-4-(2-tetrahydropyranyloxy)-2-(2-methylpropyl)hexanoylamino]propionate The product of Example 8 (0.30 g., 0.64 mmol) and benzyl beta-alanine hydrochloride (0.15 g., 0.70 mmol) were combined in 5 ml. CH$_2$Cl$_2$ at 0° C. N-Methylmorpholine (0.154 ml., 1.41 mmol) was added with stirring, followed by diethyl cyanophosphonate (0.109 ml., 0.70 mmol). After stirring 16 hours at 0° and 1 hour at room temperature, the mixture was stripped to dryness, and the residue taken up in ethyl acetate (20 ml.), extracted 2×20 ml. saturated NaHCO$_3$, 1×20 ml. H$_2$O and 1×20 ml. brine, dried (MgSO$_4$) and stripped to 0.394 g. of crude product, chromatographed on 45 g. of silica gel with 99:1 CHCl$_3$:CH OH as eluant to produce purified present title product, 0.30 g.; tlc Rf 0.8 (19:1:CHCl$_3$:CH$_3$OH).

EXAMPLE 85

Benzyl 3-[2R,4S,5S-6-Cyclohexyl-5-(t-butoxycarbonylamino)-4-hydroxy-2-(2-methylpropyl)hexanoylamino]propionate The product of the preceding Example (300 mg.) was stirred with 10 ml. 4:1 acetic acid:H$_2$O for 16 hours, stripped under high vacuum and chased with toluene to yield title product, 273 mg.

EXAMPLE 86

Benzyl 3-[2R,4S,5S-6-Cyclohexyl-5-amino-4-hydroxy-2-(2-methylpropyl)hexanoylamino]propionate Hydrochloride The product of the preceding Example (273 mg.) was dissolved in 3 ml. of ether and treated with 3 ml. 3.7N HCl in dioxane at 0° C. After 4 hours at 0°, the reaction was stripped and triturated with ether-hexane to yield title product as white solids, 248 mg.

EXAMPLE 87

Benzyl 3-[2R,4S,5S-6-Cyclohexyl-5-[N-alpha-N-(t-butoxycarbonyl)phenylalanyl)-N(imidazole)-(t-butoxycarbonyl)-histidyl]amino-4-hydroxy-2-(2-methylpropyl)hexanoylamino]propionate Except to use 39:1 CHCl$_3$:CH$_3$OH as eluant on chromatography, the method of Example 84 was used to couple the product of the preceding Example (248 mg, 0.589 mmol) and the product of Preparation 1 (357 mg., 0.707 mmol) in the presence of N-methylmorpholine (0.155 ml., 1.413 mmol) and diethyl cyanophosphonate (0.11 ml., 0.707 mmol), thereby producing purified title product, 0.225 g.; tlc 0.5 (9:1 CHCl$_3$:CH$_3$OH).

EXAMPLE 88

Benzyl 3-[2R,4S,5S-6-Cyclohexyl-5-[N-(t-butoxycarbonyl)-phenylalanylhistidyl]amino-4-hydroxy-2-(2-methylpropyl)hexanoylamino]propionate By the method of Example 85, the product of the preceding Example (342 mg.) was converted to present title product, 305 mg.; tlc Rf 0.2 (9:1 $CHCl_3:CH_3OH$).

EXAMPLE 89

3-[2R,4S,5S-6-Cyclohexyl-5-[N-(t-butoxycarbonyl)-phenylalanylhistidyl]amino-4-hydroxy-2-(2-methylpropyl)hexanoylaminopropionic Acid Using 10 ml. of pure methanol as solvent, the product of the preceding Example (0.305 g.) was hydrogenated according to Example 13. Following catalyst recovery the filtrate was stripped to yield present title product, 0.234 g.; $^1$H-nmr ($CDCl_3$) includes delta 1.5 ppm (s, 9H).

EXAMPLE 90

2R,4S,5S-6-Cyclohexyl-5-(t-butoxycarbonylamino)-4hydroxy-2-2-methyl-2-propenyl)-N-methylhexanamide The trans(2R) title product of Example 4 (0.20 g., 0.55 mmol) was dissolved in 10 ml. $CH_3OH$, cooled to 0° C., and the solution saturated with $CH_3NH_2$. After holding at 0° for 60 hours, the mixture was stripped and the solid residue triturated with hexane to yield title product, 0.220 g.

EXAMPLE 91

2R,4S,5S-6-Cyclohexyl-5-amino-4-hydroxy-2-(2-methyl-2-propenyl)-N-methylhexanamide Product of the preceding Example (0.220 g.) was stirred with 2 ml. of trifluoroacetic acid at −11° C. for 0.5 hour. The reaction mixture was stripped and the residue taken up in 5 ml. ethyl acetate, washed with 5 ml. saturated $NaHCO_3$ and 5 ml. of brine, dried ($MgSO_4$) and stripped to yield title product, 0.169 g.

EXAMPLE 92

2R,4S,5S-6-Cyclohexyl-5-[N-alpha-(N-(t-butoxycarbonylphenylalanyl)-N(imidazole)-t-butoxycarbonyl)-histidyl]amino-4-hydroxy-2-2-methyl-2-propenyl)-propenyl N-methylhexanamide The product of the preceding Example (169 mg., 0.57 mmol) and the product of Preparation 1 (288 mg., 0.57 mmol) were combined in 15 ml. $CH_2Cl_2$ with 1-hydroxybenzotriazole (77 mg., 0.57 mmol) and dicyclohexylcarbodiimide (118 mg., 0.57 mmol) at 0°. After stirring at ambient temperature for 18 hours, dicyclohexyl urea was recovered by filtration, the filtrate stripped, and the resulting residue taken up in 10 ml. ethyl acetate, washed 1×5 ml. saturated $NaHCO_3$, 1×5 ml. 5% HCl and 1×5 ml brine, dried ($MgSO_4$), stripped (0.329 g.) and chromatographed on 35 g. silica gel with 40:1 $CHCl_3:CH_3OH$ as eluant to yield purified title product, 0.129 g.

EXAMPLE 93

2R,4S,5S-6-Cyclohexyl-5-[N-(t-butoxycarbonyl)-phenylalanylhistidyl]amino-4-hydroxy-2-(2-methyl-2-propenyl)-N-methylhexanamide By the method of Example 85, with final trituration of the solid product with ether, the product of the preceding Example (0.129 g.) was converted to present title product, 75 mg.; $^1$H-nmr ($CDCl_3$) includes delta 1.5 ppm (s, 9H).

EXAMPLE 94

Ethyl 4-[2R,4S,5S-Cyclohexyl-5-(t-butoxycarbonylamino)-4-(2-tetrahydropyranyloxy)-2-(2-methylpropylhexanoylamino]butyrate Without chromatography, the method of Example 84 was employed to couple the product of Example 8 (300 mg., 0.64 mmol) with ethyl 4-aminobutyrate hydrochloride (118 mg., 0.70 mmol) to yield title product, 385 mg.

EXAMPLE 95

Ethyl 4-[2R,4S,5S-6-Cyclohexyl-5-(t-butoxycarbonylamino)-4-hydroxy-2-(2-methylpropyl)hexanoylamino]butyrate The product of the preceding Example (0.385 g.) was treated with 4:1 acetic acid:$H_2O$ according to Example 85, crude, lactone containing product (330 mg.) was isolated by freeze drying and title product isolated by chromatography on silica gel, eluting lactone with 1:1 ether:hexane and title product with 19:1 $CHCl_3.CH_3OH$, 161 mg.; tlc Rf 0.6 (9:1 $CHCl_3:CH_3OH$).

EXAMPLE 96

Ethyl 4-[2R,4S,5S-6-Cyclohexyl-5-amino-4-hydroxy-2-(2-methylpropyl)hexanoylamino]butyrate Hydrochloride The product of the preceding Example (0.161 g.) was dissolved in 5 ml. ether and cooled to 0° C. 7.4N HCl in dioxane (3 ml.) was added and the mixture stirred at 0° C. for 3.5 hours, then stripped and dried under high vacuum to yield title product, 0.141 g., tlc Rf 0.1 (9:1 $CHCl_3:CH_3OH$).

EXAMPLE 97

Ethyl 4-[2R,4S,5S-6-Cyclohexyl-5-[N-alpha-(N-(t-butoxycarbonyl)phenylalanyl)-N(imidazole)-(t-butoxycarbonyl)-histidyl]amino-4-hydroxy-2-(2-methylpropyl)hexanoylamino]butyrate By the method of Example 87, the product of the preceding Example (140 mg., 0.323 mmol) and the product of Preparation 1 (179 mg., 0.355 mmol) were coupled, isolated and purified to yield title product, 136 mg. By the method of Example 88, this product was converted to ethyl 4-[2R,4S,5S-6-cyclohexyl-5-[N-(t-butoxycarbonyl)phenylalanyl-histidyl]amino-4-hydroxy-2-(2methylpropyl)hexanoylamino]butyrate.

EXAMPLE 98

2R,4S,5S-6-Cyclohexyl-5-(t-butoxycarbonylamino)-2-(p-chlorobenzyl)-gamma-hexanolactone By the method of Example 39, the less polar 4S,5S-product of Example 3 (2.5 g., 0.008 mol) and 4-chlorobenzyl bromide (1.81 g., 0.0088 mol) were converted to present chromatographed title product as a colorless gum, 1.91 g.; tlc Rf 0.6 (3:1 hexane:ethyl acetate) 0.7 (2:1 hexane:ethyl acetate with 1% acetic acid).

EXAMPLE 99
2R,4S,5S-6-Cyclohexyl-5-(t-butoxycarbonylamino)-2-(p-methylbenzyl)-gamma-hexanolactone Using 5:1 hexane:ethyl acetate as eluant on chromatography, the method of Example 39 was used to convert the 4S,5S product of Example 3 (1.5 g., 0.0048 mol) and alpha-bromo-p-xylene (0.98 g., 0.0053 mol) to present title product as a white gum, 0.985 g.; tlc Rf 0.55 (2:1 hexane:ethyl acetate), 0.75 (1:1 hexane:ethyl acetate).

EXAMPLE 100
2R,4S,5S-6-Cyclohexyl-5-(t-butoxycarbonylamino)-2-(p-methoxybenzyl)-gamma-hexanolactone By the method of Example 99, the 4S,5S-product of Example 3 (3.79 g., 0.0118 mol) and p-methoxybenzyl-bromide (2.61 g., 0.130 mol) were converted to chromatographed title product, as a white gum, 1.06 g.; tlc Rf 0.4 (3:1 hexane:ethyl acetate).

EXAMPLE 101
2R,4S,5S-6-Cyclohexyl-5-t-butoxycarbonylamino)-2-(3,4-dichlorobenzyl)-gamma-hexanolactone By the method of Example 39, using 3:1 hexane:ethyl acetate as eluant on chromatography, the 4S,5S-product of Example 3 (2.0 g., 0.0064 mol) and 3,5-dichlorobenzyl bromide (1.68 g., 0.007 mol) were converted to title product as a clear gum, 1.36 g.; tlc Rf 0.22 (3:1 hexane:ethyl acetate), 0.9 (1:2 hexane:ethyl acetate with 1% acetic acid).

EXAMPLE 102
2R,4S,5S-6-Cyclohexyl-5-(t-butoxycarbonylamino)-2-(o-chlorobenzyl)-gamma-hexanolactone By the method of Example 39, using 6:1 hexane:ethyl acetate as eluant on chromatography, the 4S,5S-product of Example 3 (2.0 g., 0.0064 mol) and o-chlorobenzyl chloride (1.44 g., 0.007 mol) were converted to title product as a clear gum, 1.51 g.; tlc Rf 0.75 (3:1 hexane:ethyl acetate), 0.65 (2:1 hexane:ethyl acetate with 1% acetic acid).

EXAMPLE 103
2R,4S,5S-6-Cyclohexyl-5-(t-butoxycarbonylamino)-2-(m-chlorobenzyl)-gamma-hexanolactone By the method of the preceding Example, 4S,5S-product of Example 3 (2.0 g., 0.0064 mol) and m-chlorobenzyl chloride (0.92 ml., 1.44 g., 0.007 mol) were converted to chromatographed title product as a colorless gum, 2.11 g.; tlc Rf 0.4 (3:1 hexane:ethyl acetate), 0.75 (2:1 hexane:ethyl acetate with 1% acetic acid).

EXAMPLE 104
2R,4S,5S-6-Cyclohexyl-5-(t-butoxycarbonylamino)-4-hydroxy-2-(p-chlorobenzyl)-N-methylhexanamide Using a reaction time of 2 hours at ambient temperature, without hexane trituration, the procedure of Example 90 was used to convert the product of Example 98 (1.0 g.) to present title product as white solids, 1.07 g.; tlc Rf 0.75 (2:1 hexane:ethyl acetate with 1% acetic acid), 0.6 (18:2:1 $CH_2Cl_2:C_2H_5OH$:acetic acid).

EXAMPLE 105
2R,4S,5S-6-Cyclohexyl-5-(t-butoxycarbonyl)-4-hydroxy-2-(p-methylbenzyl)-N-methylhexanamide Using the method of the preceding Example, chromatographing the product on silica gel with 1:1 hexane:ethyl acetate as eluant, the product of Example 99 (0.885 g.) was converted to present title product, 0.518 g.; tlc Rf 0.1 (1:1 ethyl acetate:hexane), 0.55 (18:2:1 $CHCl_3:C_2H_5OH$:acetic acid).

EXAMPLE 106
2R,4S,5S-6-Cyclohexyl-5-(t-butoxycarbonylamino)-4-hydroxy-2-(p-methoxybenzyl)-N-methylhexanamide By the method of Example 4, the product of Example 100 (1.06 g.) was converted to present title product as off-white solids, 1.07 g.; tlc Rf 0.2 (2:1 ethyl acetate:hexane with 1% acetic acid), 0.8 (9:1 $CH_2Cl_2:C_2H_5OH$ with 1% concentrated $NH_4OH$).

EXAMPLE 107
2R,4S,5S-5-Cyclohexyl-4-(t-butoxycarbonylamino)-4-hydroxy-2-(3,4-dichlorobenzyl)-N-methylhexanamide By the method of Example 104, the product of Example 101 (1.36 g.) was converted to present product as a white gum, 1.39 g.; tlc Rf 0.25 (1:1 hexane:ethyl acetate with 1% acetic acid), 0.55 (9:1 $CH_2Cl_2:C_2H_5OH$ with 1% concentrated $NH_4OH$.

EXAMPLE 108
2R,4S,5S-6-Cyclohexyl-5-(t-butoxycarbonylamino)-4-hydroxy-2-(o-chlorobenzyl)-N-methylhexanamide Except to use a reaction time of 16 hours at ambient temperature, the method of Example 104 was used to convert the product of Example 102 (1.51 g.) to present product as a white gum, 1.56 g.; tlc Rf 0.09 (2:1 hexane:acetic acid with 1% acetic acid).

EXAMPLE 109
2R,4S,5S-6-Cyclohexyl-5-(t-butoxycarbonylamino)-4-hydroxy-2-(m-chlorobenzyl)-N-methylhexanamide By the method of Example 104, the product of Example 103 (2.11 g.) was converted to present title product as a white gum, 1.68 g.; tlc Rf 0.25 (2:1 hexane:ethyl acetate with 1% acetic acid), 0.5 (9:1 $CH_2Cl_2:C_2H_5OH$ with 1% acetic acid).

EXAMPLE 110
2R,4S,5S-6-Cyclohexyl-5-amino-4-hydroxy-2-(p-chlorobenzyl)-N-methylhexanamide Hydrochloride The product of Example 104 (1.07 g.) was stirred under $N_2$ in 10 ml. of 3.78N HCl in dioxane for 10 minutes, stripped. The residue was 3 times combined with 10 ml. of ether and restripped, producing title product as a solid, 1.11 g., tlc Rf 0.18 (18:2:1 $CH_2Cl_2:C_2H_5OH$:acetic acid).

EXAMPLE 111
2R,4S,5S-6-Cyclohexyl-5-amino-4-hydroxy-2-(p-methylbenzyl)-N-methylhexanamide Hydrochloride By the method of the preceding Example, the product of Example 105 (0.454 g.) was converted to present title product, 0.4 g., tlc Rf 0.1 (18:2:1 $CHCl_3:C_2H_5OH$:acetic acid).

EXAMPLE 112

2R,4S,5S-6-Cyclohexyl-5-amino-4-hydroxy-2-(p-methoxybenzyl)-N-methylhexanamide Hydrochloride By the method of Example 110, the product of Example 106 (1.07 g.) was converted to present title product in quantitative yield (weight yield 1.14 g., 0.22 g., greater than theory); tlc Rf 0.2 (9:1 $CH_2Cl_2:C_2H_5OH$ with 1% concentrated $HN_4OH$).

EXAMPLE 113

2R,4S,5S-6-Cyclohexyl-5-amino-4-hydroxy-2-(3,4-dichlorobenzyl)-N-methylhexanamide Hydrochloride By the method of Example 110, the product of Example 107 (1.38 g.) was converted to present title product in quantitative yield (weight 1.52 g., 0.30 g. greater than theory); tlc Rf 0.25 ($CH_2Cl_2:C_2H_5OH$ 9:1 with 1% concentrated $NH_4OH$).

EXAMPLE 114

2R,4S 5S-6-Cyclohexyl-5-amino-4-hydroxy-2-(o-chlorobenzyl)-N-methylhexanamide Hydrochloride By the method of Example 110, the product of Example 108 (1.56 g.) was converted to present title product, 1.4 g.; tlc Rf 0.1 (9:1 $CH_2Cl_2:C_2H_5OH$ with 1% acetic acid).

EXAMPLE 115

2R,4S,5S-6-Cyclohexyl-5-amino-4-hydroxy-2-(m-chlorobenzyl)-N-methylhexanamide Hydrochloride By the method of Example 110, the product of Example 109 (1.67 g.) was converted to present title product in quantitative yield (0.23 g. greater than theory); tlc 0.1 (9:1 $CH_2Cl_2:C_2H_5$ with 1% acetic acid).

EXAMPLE 116

2R,4S,5S-6-Cyclohexyl-5-[N-(t-butoxycarbonyl)-phenylalanyl-N(imidazole)-t-butoxycarbonyl)histidyl-]amino-4-hydroxy-2-(p-chlorobenzyl)-N-methylhexanamide Under nitrogen the product of Example 110 (1.11 g., 0.0023 mol) was stirred with 8 ml. $CH_2Cl_2$. Added in sequence were triethylamine (0.42 ml., 0.0030 mol), the product of Preparation 1 (1.20 g., 0.0024 mol), 1-hydroxybenzotriazole (0.583 g., 0.0038 mol) and dicyclohexylcarbodiimide (0.495 g., 0.0024 mol) and the mixture stirred for 24 hours. The reaction mixture was diluted with 25 ml. $CH_2Cl_2$, washed with 2×12 ml. 1N NaOH and 1×12 ml. saturated NaCl, dried ($Na_2SO_4$) and stripped to a foam, 1.31 g. The latter was chromatographed on silica gel with 19:1 $CH_2Cl_2:C_2H_5OH$ as eluant to yield purified title product, 0.70 g.; tlc Rf 0.65 (18:2:1 $CH_2Cl_2:C_2H_5OH$:acetic acid).

EXAMPLE 117

2R,4S,5S-6-Cyclohexyl-5-[N-(t-butoxycarbonyl)-phenylalanyl-N(imidazole)-(t-butoxycarbonyl)histidyl-]amino-4-hydroxy-2-(p-methylbenzyl)-N-methylhexanamide Except to combine the reagents at 0° C., then allowing the reaction mixture to warm, and to use 5:1 $CH_2Cl_2:C_2H_5OH$ as eluant on chromatography, the method of the preceding Example was used to convert the product of Example 111 (0.4 g.) to present title product, 0.60 g.; tlc Rf 0.9 (18:2:1 $CH_2Cl_2:C_2H_5OH$:acetic acid).

EXAMPLE 118

2R,4S,5S-6-Cyclohexyl-5-[N-(t-butoxycarbonyl)-phenylalanyl-N(imidazole)-(t-butoxycarbonyl)histidyl-]amino-4-hydroxy-2-(p-methoxybenzyl)-N-methylhexanamide By the method of the preceding Example, using 20:1 $CH_2Cl_2:C_2H_5OH$ as eluant on chromatography, the product of Example 112 (0.92 g., corrected for purity) was converted to present title product as a white solid, 0.73 g.; tlc Rf 0.7 (9:1 $CH_2Cl_2:C_2H_5OH$, 0.85 (9:1 $CH_2Cl_2:CH_3OH$ with 1% concentrated $NH_4OH$).

EXAMPLE 119

2R,4S,5S-6-Cyclohexyl-5-[N-(t-butoxycarbonyl)-phenylalanyl-N(imidazole)-(t-butoxycarbonyl)histidyl-]amino-4-hydroxy-2-(3,4-dichlorobenzyl)-N-methylhexanamide By the method of Example 117, using 24:1 $CH_2Cl_2:C_2H_5OH$ as eluant on chromatography, the product of Example 113 (1.22 g., corrected for purity) was converted to present product, 1.08 g.; tlc Rf 0.75 (9:1 $CHCl_3:C_2H_5OH$).

EXAMPLE 120

2R,4S,5S-6-Cyclohexyl-5-[N-(t-butoxycarbonyl)-phenylalanyl-N(imidazole)-(t-butoxycarbonyl)histidyl-]amino-4-hydroxy-2-(o-chlorobenzyl)-N-methylhexanamide By the method of Example 119, the product of Example 114 (1.33 g., corrected for purity) was converted to chromatographed title product as a white solid, 1.02 g.; tlc Rf 0.55 (9:1 $CH_2Cl_2$:ethyl acetate with 1% acetic acid).

EXAMPLE 121

2R,4S,5S-6-Cyclohexyl-5-[N-(t-butoxycarbonyl)-phenylalanyl-N(imidazole)-(t-butoxycarbonyl)histidyl-]amino-4-hydroxy-2-(m-chlorobenzyl)-N-methylhexanamide By the method of Example 119, the product of Example 115 (1.45 g., corrected for purity) was converted to chromatographed title product as a white gum, 1.68 g.; tlc Rf 0.62 (9:1 $CH_2Cl_2:C_2H_5OH$ with 1% acetic acid).

EXAMPLE 122

2R,4S,5S-6-Cyclohexyl-5-t-butoxycarbonylphenylalanyl-histidyl)amino-4-hydroxy-2-(p-chlorobenzyl)-N-methylhexanamide The product of Example 116 (0.25 g.) was combined with 2 ml. glacial acetic acid and 0.5 ml. $H_2O$ and stirred under $N_2$ for 8 hours, then stripped to dryness, and the residue triturated 3×0.5 ml. toluene, then slurried 3 x 5 ml. ether, restripping each time, to yield 83 mg. of crude product. The latter was purified on 5 g. of bonded phase - octadecylsilane ($C_{18}$) reverse phase packing in a 10 mm i.d. flash column with 1:1 $CH_3OH$:$H_2O$ as the initial mobile phase. The crude was dissolved in 2 ml. 1:1 $CH_3OH:H_2O$, filtered and applied to the column. The column was eluted with 4 column volumes 1:1 $CH_3OH:H_2O$, 2 column volumes 6:4 $CH_3OH:H_2O$, 2 column volumes 7:3 $CH_3OH:H_2O$, 2 column volumes 8:2 $CH_3OH:H_2O$ to remove more polar impurities. Title product came off in 2 column volumes of 9:1 CH₃OH:H₂O, recovered as white solids, 30 mg.; ¹H-nmr (300 MHz, DMSO-d₆) includes delta (ppm) 1.28 (s, 9H, t-butyl) and 6.99 (d, J=7 Hz, 1H, imidazole hydrogen).

EXAMPLE 123

2R,4S,5S-6-Cyclohexyl-5-(t-butoxycarbonylphenylalanyl-histidyl)amino-4-hydroxy-2-(p-methylbenzyl)-N-methylhexanamide By the method of the preceding Example, except that product eluted a little later, in 2 column volumes of 100% CH₃OH, the product of Example 117 (100 mg.) was converted to purified title product as white solids, 41 mg.; ¹H-nmr (300 MHz, DMSO-d₆) delta (ppm) includes 1.25 (s, 9H, t-butyl), 6.83 (d, J=12 Hz, 1H, imidazole hydrogen).

EXAMPLE 124

2R,4S,5S-6-Cyclohexyl-5-(t-butoxycarbonylphenylalanyl-histidyl)amino-4-hydroxy-2-(p-methoxybenzyl)-N-methylhexanamide By the method of the preceding Example, the product of Example 118 (0.362 g.) was converted to present purified title product as white solids, 0.126 g.; tlc Rf 0.55 (9:1 CH₂Cl₂:CH₃OH with 1% concentrated NH₄OH); ¹H-nmr (300 MHz, DMSO-d₆) delta (ppm) includes 1.27 (s, 9H, t-butyl), 2.42 [d, J=4 Hz, 3H, NCH₃) and 3.66 (s, 3H, OCH₃).

EXAMPLE 125

2R,4S,5S-6-Cyclohexyl-5-(t-butoxycarbonyl-phenylalanyl-histidyl)amino-4-hydroxy-2-(3,4-dichlorobenzyl)-N-methylhexanamide By the method of Example 122, without chromatography, the product of Example 119 (1.08 g.) was converted to present title product as white solids, 0.90 g.; ¹H-nmr (300 MHz, DMSO-d₆) delta (ppm) includes 1.29 (s, 9H, t-butyl), 2.47 (d, J=5 Hz, 3H, NCH₃).

EXAMPLE 126

2R,4S,5S-6-Cyclohexyl-5-t-butoxycarbonylphenylalanyl-histidyl)amino-4-hydroxy-2-(o-chlorobenzyl)-N-methylhexanamide By the procedure of the preceding Example, the product of Example 120 (1.01 g.) was converted to crude title product (0.48 g.), purified by chromatography on silica gel using 9:1 CH₂Cl₂:CH₃OH as eluant, 0.22 g.; tlc Rf 0.5 (9:1 CH₂Cl₂:CH₃OH with 1% concentrated NH₄OH); ¹H-nmr (300 MHz, DMSO-d₆) delta (ppm) includes 1.27 (s, 9H, t-butyl), 2.45 (d, J=4 Hz, 3H, NCH₃).

EXAMPLE 127

2R,4S,5S-6-Cyclohexyl-5-(t-butoxycarbonylphenylalanyl-histidyl)amino-4-hydroxy-2-(m-chlorobenzyl)-N-methylhexanamide By the procedure of the preceding Example, the product of Example 121 (0.94 g.) was converted to chromatographed title product as white solids, 0.58 g.; tlc Rf 0.15 (9:1 CH₂Cl₂:C₂H₅OH with 1% acetic acid); ¹H-nmr (300 MHz, DMSO-d₆) delta (ppm) includes 1.27 (s, 9H, t-butyl), 2.45 (d, J=5 Hz, 3H, NCH₃).

PREPARATION 1

N-alpha-[N-t-Butoxycarbonylphenylalanyl]-N(imidazole)-(t-butoxycarbonyl)histidine A slurry of 36.4 g. L-histidine methyl ester dihydrochloride in dichloromethane 1000 ml.) was cooled to 5° and treated with 52 ml. triethylamine. After 10 minutes 40 g. t-butoxycarbonyl-phenylalanine was added followed by 1-hydroxybenzotriazole (30.6 g.) and, after another 5 minutes, dicyclohexylcarbodiimide (30.8 g.). The mixture was then filtered and washed with dichloromethane. The combined filtrate and wash liquor was stripped and the residue was dissolved in 1000 ml. ethyl acetate. After 10 minutes of stirring the mixture was filtered and the filtrate was washed with 1N NaOH (3×150 ml.) and brine, dried over MgSO₄, and concentrated giving 45.9 g. of intermediate t-butoxycarbonyl-phenylalanyl-histidine methyl ester as a colorless solid. Without further purification, 40 g. of this intermediate solid was dissolved in 600 ml. methanol and 200 ml. water was added. The mixture was chilled to 0° and treated with 40 g. anhydrous potassium carbonate, stirred at 15°–20° for 2.5 hours then at 28° for 1.5 hours, cooled to 10°, and adjusted to pH 4.2 with 12N HCl. The resulting solution was concentrated to about 250 ml. and 70 ml. water was added, followed by 660 ml. dioxane. At 0° the pH was brought to 13.5 and 29 ml. di-(t-butyl)dicarbonate was added. After 30 minutes (during which time the temperature was raised to 20°) the pH had dropped to 9.5, and 10 ml. di-(t-butyl)dicarbonate was added. After another 1 hour the pH was 8.0 and the reaction was complete. The mixture was concentrated to remove dioxane, 300 ml. water was added, and the mixture was washed twice with ether. Ethyl acetate (500 ml.) was added and at 10° the pH was brought to 1.2 with conc. HCl. The organic layer was separated and the aqueous layer was washed twice with ethyl acetate. The ethyl acetate layers were combined, washed with water, brine, dried over Na₂SO₄, and concentrated to give after several coevaporations with ether and drying at 25° C. to constant weight a colorless foam, weight 44 g. HPLC at 60/40 MeCN/pH 2.1 0.1M phosphate on Zorbax 25 cm×4.6 mm at 214 nm, 1.5 ml/min., retention time 3.23 minutes (94% of the total absorbance to 10 minutes); ¹H-nmr (CDCl₃) ppm: 1.40 (s, 9H, C(CH₃)₃), 1.60 (s, 9H, C(CH₃)₃), 3.0-3.4 (m, 4H, CH₂), 4.40 (m, 1H), 4.71 (m, 1H), 5.32 (m, 1H), 6.89 (br, 1H), 8.13 (s, 1H), 7.1–7.4 m, 7H).

PREPARATION 2

1,5-Di(benzyloxycarbonylamino)pentane

Under N₂, 1,5-diaminopentane (2.86 ml., 2.5 g., 0.0245 mol) was dissolved in 50 ml. CH₂Cl₂ and cooled to 0°. With stirring, benzyloxycarbonyl chloride (3.67 ml., 4.17 g., 0.0245 mol) was added dropwise, maintaining the temperature near 0°. The mixture was warmed to room temperature, washed 2×50 ml. 5% HCl, 1×50 ml. saturated NaHCO₃, and 1×50 ml. brine, dried (MgSO₄) and stripped to yield title product as a white solid, 4 g.; ¹H-nmr (CDCl₃) includes delta 5.2 ppm (s, 4H, two benzyl CH₂ groups). The yield is greatly enhanced by use of two molar equivalents of the acid chloride.

PREPARATION 3

5-(Benzyloxycarbonylamino)pentylamine Hydrobromide

Under nitrogen, the product of the preceding Preparation (4.0 g., 0.0108 mol) was slurried in $CH_2Cl_2$ (11 ml.) and ether (5.4 ml.). 30% HBr in acetic acid (2.7 ml.) was added with stirring. Solids began to precipitate from the resulting solution within 2 minutes. After 20 minutes, 5 ml. ether was added and title product recovered by filtration with ether wash, 2.7 g., $^1$H-nmr ($CD_3OD$) includes delta 5.2 ppm (s, 2H, benzyl $CH_2$).

PREPARATION 4

N-alpha-Methylhistidine Methyl Ester Dihydrochloride

N-alpha-Methylhistidine (Reinhold et al., J. Med. Chem. 11, p. 258, 1968, 4.0 g., 0.0195 mol) was slurried in 40 ml. methanol at 0°, sparged with dry HCl for 8 minutes (solution occurred after 3 minutes), heated to reflux for 4 hours, and co-stripped with ether to yield title product as a white powder, 4.94 g.

PREPARATION 5

N-alpha-Methyl-N-alpha-[N-(t-butoxycarbonyl)-phenylalanyl)histidine Methyl Ester The product of the preceding Preparation (1.6 g., 0.0087 mol), N-(t-butoxycarbonyl)phenylalanine (2.55 g., 0.096 mol), 1-hydroxybenzotriazole (2.44 g., 0.016 mol) and dicyclohexylcarbodiimide (1.98 g., 0.0096 mol) were combined in 10 ml. of $CH_2Cl_2$ at 0° for 4 hours. The reaction mixture was diluted with 10 ml. fresh $CH_2Cl_2$, filtered to yield a first solid, the filtrate stripped, the residue taken up in 15 ml. ethyl acetate, refiltered to yield a second solid, the second filtrate washed 2×7.5 ml. 1N NaOH, 1×7.5 ml. $H_2O$, a third solid removed by filtration after cooling to 0°, and the third filtrate concentrated to dryness and the residue triturated with ethyl acetate to form a fourth solid. The first and second solids (DCU) were discarded The third and fourth solids, containing very little DCU, were combined to yield 2.47 g. of title product.

PREPARATION 6

N-alpha-Methyl-N-alpha-[N-t-butoxycarbonyl)-phenylalanyl]histidine

The product of the preceding Preparation (2.32 g., 0.054 mol) in 70 ml. acetone and 20 ml. $H_2O$ was hydrolyzed for 3.5 hours with 1.1N NaOH (5.4 ml., 1.1 equivalents). The acetone was stripped and the aqueous residue adjusted to pH 5.8 with dilute HCl. The resulting solution of title product was employed without isolation in the next step.

PREPARATION 7

N-alpha-Methyl-N-alpha-[N-t-butoxycarbonyl)-phenylalanyl-N(imidazole)-(t-butoxycarbonyl)histidine The entire solution of product from the preceding Preparation was diluted to 30 ml. with $H_2O$ and further diluted with 30 ml. dioxane, and cooled to 0°. The pH was adjusted to 11.0 with dilute NaOH and di(t-butoxycarbonyl)anhydryde [(t-boc)$_2$O; 1.61 ml., 0.007 mol, ca. b 1.3 equivalents) added, and the temperature maintained at 0° for 1 hour while maintaining pH 8.5–11.0 by the addition of dilute NaOH. The bath was removed, an additional 0.5 ml. of the anhydride was added and the pH quickly stabilized at 10.5. The dioxane was stripped and the aqueous residue washed 2×30 ml. ethyl acetate. The combined organic layers were back washed 1×30 ml. $H_2O$ and the wash combined with the original aqueous layer, covered with 50 ml. fresh ethyl acetate, and the pH adjusted to 1.4 with dilute HCl. The acid ethyl acetate layer was separated combined with a further 30 ml. ethyl acetate wash of the acidic aqueous layers, back washed with 30 ml. fresh $H_2O$, dried over $Na_2SO_4$ and co-stripped with ether to yield title product, 1.9 g.

PREPARATION 8

N-alpha-(2-Benzyl-3-phenylpropionyl)histidine Methyl Ester

Under nitrogen 2-benzyl-3-phenylpropionic acid (dibenzylacetic acid, 5.0 g., 0.0208 mol) and histidine methyl ester dihydrochloride (4.72 g., 0.0208 mol) were combined in 100 ml. $CH_2Cl_2$ and cooled to 0°. Dicyclohexylcarbodiimide (4.29 g., 0.0208 mol) and then N-methylmorpholine (4.58 ml., 0.0416 mol) were added and the mixture stirred, allowed to warm to ambient temperature and stirred for 16 hours. Insolubles were removed by filtration, filtrate washed 2×100 $H_2O$, 2×100 ml. saturated $NaHCO_3$ and 1×100 ml. brine, dried over $MgSO_4$, stripped to a residue weighing 6.8 g., and the residue chromatographed on 600 g. of silica gel with 99:1 $CHCl_3$:$CH_3OH$ as eluant to produce purified title product, 4.5 g.; $^1$H-nmr ($CDCl_3$) delta includes delta 3.8 (s, 3H, $OCH_3$).

PREPARATION 9

N-alpha-(2-Benzyl-3-phenylpropionyl)-N(imidazole)(t-butoxycarbonyl)histidine Title product of the preceding Preparation (4.5 g., 0.0108 mol) and $K_2CO_3$ (4.66 g., 0.0378 mol) were combined in 25 ml. $CH_3OH$ and 8 ml. $H_2O$ and stirred 16 hours. The methanol was stripped and the aqueous residue diluted with 25 ml. dioxane and 15 ml. of $H_2O$. Di-(t-butyl)dicarbonate (2.8 g., 0.013 mol) and the mixture stirred 16 hours. The dioxane was stripped and the basic aqueous residue extracted with 20 ml. ether, adjusted to pH 2.5 with 5% HCl and extracted 30 ml. of fresh ether. The latter organic layer was washed with brine, dried over $MgSO_4$, stripped, the residue triturated with 15 ml. 1:1 ether:hexane and filtered to yield title product, 1.6 g.; $^1$H-nmr ($CDCl_3$) includes delta 1.6 (s, 9H, $C(CH_3)_3$).

We claim:

1. A compound of the formula

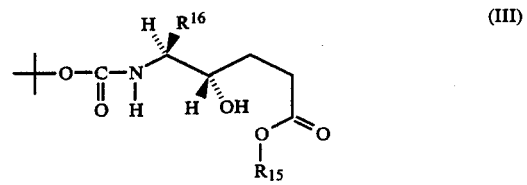

(III)

wherein $R^{15}$ is $(C_1-C_3)$alkyl; and $R^{16}$ is $(C_1-C_6)$alkyl, $(C_1-C_6)$alkenyl, phenyl, naphthyl, $(C_4-C_7)$cycloalkyl, $(C_4-C_7)$cycloalkenyl, $C_7-C_9)$phenylalkyl, $(C_{11}-C_{13})$naphthylalkyl, $(C_5-C_{10})$(cycloalkyl)alkyl, or one of said groups mono or disubstituted on the aromatic ring with the same or different groups selected from $(C_1-C_3)$alkyl, $(C_1-C_3)$alkoxy, fluoro or chloro.

2. A compound of claim 1 wherein $R^{16}$ is cyclohexylmethyl.

3. The compound of claim 2 wherein $R^{15}$ is ethyl.

* * * * *